US012778737B2

(12) United States Patent
Heftman et al.

(10) Patent No.: US 12,778,737 B2
(45) Date of Patent: Nov. 3, 2026

(54) METHODS AND DEVICES FOR URETHRAL TREATMENT

(71) Applicant: PROARC MEDICAL LTD., Yokne'am Illit (IL)

(72) Inventors: Gilad Heftman, Pardes Hana-Karkur (IL); Eran Hason, Pardes Hana-Karkur (IL); David Nitsan, Tel Aviv (IL)

(73) Assignee: PROARC MEDICAL LTD., Yokne'am Illit (IL)

( * ) Notice: Subject to any disclaimer, the term of this patent is extended or adjusted under 35 U.S.C. 154(b) by 1003 days.

(21) Appl. No.: 18/000,759

(22) PCT Filed: Jun. 9, 2021

(86) PCT No.: PCT/IB2021/055063
§ 371 (c)(1),
(2) Date: Dec. 5, 2022

(87) PCT Pub. No.: WO2021/250588
PCT Pub. Date: Dec. 16, 2021

(65) Prior Publication Data

US 2023/0240829 A1 Aug. 3, 2023

Related U.S. Application Data

(60) Provisional application No. 63/036,548, filed on Jun. 9, 2020.

(51) Int. Cl.
*A61F 2/04* (2013.01)
*A61B 17/32* (2006.01)
(Continued)

(52) U.S. Cl.
CPC ........ *A61F 2/04* (2013.01); *A61B 17/320016* (2013.01); *A61F 2/88* (2013.01);
(Continued)

(58) Field of Classification Search
CPC ............... A61F 2002/047; A61B 17/32; A61B 17/320016; A61B 2017/00274
See application file for complete search history.

(56) References Cited

U.S. PATENT DOCUMENTS 3,726,279 A 4/1973 Barefoot et al.
4,660,560 A 4/1987 Klein
(Continued)

FOREIGN PATENT DOCUMENTS

EP 0125352 A1 11/1984
EP 1413262 A1 4/2004
(Continued)

OTHER PUBLICATIONS

Corrected Notice of Allowability for U.S. Appl. No. 17/533,306 mailed Jan. 31, 2024.
(Continued)

*Primary Examiner* — Rebecca S Preston
(74) *Attorney, Agent, or Firm* — Ballard Spahr LLP

(57) ABSTRACT

A device and a method for treatment of a urethra that is constricted due to benign prostatic hyperplasia (BPH) are provided, including a delivery tool (101) advanced to a location in an area of the urethra that is to be treated. The delivery tool (101) includes an expandable element (400) that expands within the urethra such as to enlarge the urethra, a tissue cutter (412) that forms a cut in the urethra, subsequently to the expandable element expanding to dilate the urethra, and an implant (410) that maintain the urethra in a dilated state. The implant (410) includes a shape-memory material and is shaped to define two end sections and a middle section (1202) disposed between the two end sections. The shape memory-material is shape set such that in an unconstrained configuration of the implant (410), the
(Continued)

middle section (1202) is substantially straight. Other embodiments are also described.

26 Claims, 23 Drawing Sheets

(51) Int. Cl.

| | |
|---|---|
| ***A61F 2/88*** | (2006.01) |
| ***A61F 2/92*** | (2013.01) |
| ***A61F 2/958*** | (2013.01) |
| *A61B 17/00* | (2006.01) |
| *A61B 18/00* | (2006.01) |
| *A61B 90/00* | (2016.01) |
| *A61F 2/95* | (2013.01) |

(52) U.S. Cl.
CPC ................ *A61F 2/92* (2013.01); *A61F 2/958* (2013.01); *A61B 2017/00274* (2013.01); *A61B 2017/00296* (2013.01); *A61B 2018/00547* (2013.01); *A61B 2018/00601* (2013.01); *A61B 2090/3614* (2016.02); *A61F 2002/047* (2013.01); *A61F 2002/9505* (2013.01); *A61F 2002/9583* (2013.01); *A61F 2210/0014* (2013.01); *A61F 2230/0091* (2013.01)

(56) References Cited

U.S. PATENT DOCUMENTS

| | | | |
|---|---|---|---|
| 5,030,227 | A | 7/1991 | Rosenbluth et al. |
| 5,133,713 | A | 7/1992 | Huang et al. |
| 5,269,802 | A | 12/1993 | Gårber |
| 5,643,340 | A | 7/1997 | Nunokawa |
| 5,674,242 | A | 10/1997 | Phan et al. |
| 5,766,203 | A | 6/1998 | Imran et al. |
| 5,921,982 | A | 7/1999 | Lesh et al. |
| 6,070,589 | A | 6/2000 | Keith et al. |
| 6,319,282 | B1 | 11/2001 | Nishi |
| 6,673,101 | B1 | 1/2004 | Fitzgerald et al. |
| 7,004,965 | B2 | 2/2006 | Gross |
| 7,279,002 | B2 | 10/2007 | Shaw et al. |
| 7,632,297 | B2 | 12/2009 | Gross |
| 8,016,845 | B1 | 9/2011 | Sauer |
| 8,145,321 | B2 | 3/2012 | Gross |
| 8,840,660 | B2 | 9/2014 | Weber |
| 10,406,333 | B2 | 9/2019 | Feld |
| 2002/0007222 | A1 | 1/2002 | Desai |
| 2002/0010489 | A1 | 1/2002 | Grayzel et al. |
| 2002/0032486 | A1 | 3/2002 | Lazarovitz et al. |
| 2002/0032488 | A1 | 3/2002 | Brekke et al. |
| 2002/0035391 | A1 | 3/2002 | Mikus et al. |
| 2002/0072761 | A1 | 6/2002 | Abrams et al. |
| 2003/0055313 | A1 | 3/2003 | Anderson et al. |
| 2003/0060870 | A1 | 3/2003 | Reever |
| 2003/0069467 | A1 | 4/2003 | Lau et al. |
| 2003/0167088 | A1 | 9/2003 | Abraham et al. |
| 2003/0191479 | A1 | 10/2003 | Thornton |
| 2003/0216814 | A1 | 11/2003 | Siegel et al. |
| 2003/0225420 | A1 | 12/2003 | Wardle |
| 2004/0030217 | A1 | 2/2004 | Yeung et al. |
| 2004/0064139 | A1 | 4/2004 | Yossepowitch |
| 2004/0181235 | A1 | 9/2004 | Daignault et al. |
| 2005/0055087 | A1 | 3/2005 | Starksen |
| 2005/0137716 | A1 | 6/2005 | Gross |
| 2005/0163821 | A1 | 7/2005 | Sung et al. |
| 2006/0095058 | A1 | 5/2006 | Sivan et al. |
| 2006/0149308 | A1 | 7/2006 | Melsheimer et al. |
| 2006/0167540 | A1 | 7/2006 | Masters et al. |
| 2006/0173517 | A1 | 8/2006 | Gross |
| 2006/0229711 | A1 | 10/2006 | Yan et al. |
| 2006/0271151 | A1 | 11/2006 | Mcgarry et al. |
| 2006/0276871 | A1 | 12/2006 | Lamson et al. |
| 2007/0093781 | A1 | 4/2007 | Kugler et al. |
| 2008/0065209 | A1 | 3/2008 | Pflueger |
| 2009/0018523 | A1 | 1/2009 | Lamson et al. |
| 2009/0156977 | A1 | 6/2009 | Daignault et al. |
| 2009/0264987 | A1 | 10/2009 | Gale |
| 2009/0297582 | A1 | 12/2009 | Meyer et al. |
| 2010/0100195 | A1 | 4/2010 | Gross |
| 2010/0130815 | A1 | 5/2010 | Sade et al. |
| 2010/0137893 | A1 | 6/2010 | Kilemnick et al. |
| 2010/0292715 | A1 | 11/2010 | Nering et al. |
| 2010/0312054 | A1 | 12/2010 | Beyar et al. |
| 2012/0010645 | A1 | 1/2012 | Feld |
| 2013/0268086 | A1 | 10/2013 | Creedon et al. |
| 2014/0012192 | A1 | 1/2014 | Bar-On et al. |
| 2016/0000455 | A1 | 1/2016 | Golan et al. |
| 2016/0096009 | A1 | 4/2016 | Feld |
| 2018/0344995 | A1 | 12/2018 | Bar-On et al. |
| 2019/0125516 | A1 | 5/2019 | Lamson et al. |
| 2019/0381291 | A1 | 12/2019 | Feld |

FOREIGN PATENT DOCUMENTS

| | | | |
|---|---|---|---|
| EP | 1415681 | A1 | 5/2004 |
| JP | 2004147812 | A | 5/2004 |
| JP | 2015144751 | A | 8/2015 |
| WO | 9404081 | A1 | 3/1994 |
| WO | 0143664 | A1 | 6/2001 |
| WO | 2007048437 | A1 | 5/2007 |
| WO | 2007109621 | A2 | 9/2007 |
| WO | 2008056194 | A1 | 5/2008 |
| WO | 2008142677 | A2 | 11/2008 |
| WO | 2010106543 | A2 | 9/2010 |
| WO | 2012123950 | A2 | 9/2012 |
| WO | 2014141278 | A1 | 9/2014 |
| WO | 2021250588 | A1 | 12/2021 |
| WO | 2024003851 | A1 | 1/2024 |

OTHER PUBLICATIONS

International Search Report and Written Opinion from International Application No. PCT/IB2023/056813 mailed Sep. 28, 2023.
Issue Notification for U.S. Appl. No. 17/533,306 mailed Feb. 21, 2024.
Non-Final Office Action for U.S. Appl. No. 16/048,481 mailed Feb. 26, 2024.
Examination Report for European Application No. 18215225.6 mailed Nov. 2, 2023.
Final Office Action for U.S. Appl. No. 16/048,481 mailed Nov. 6, 2023.
Issue Notification for U.S. Appl. No. 16/554,774 mailed Jul. 26, 2023.
Non-Final Office Action for U.S. Appl. No. 16/048,481 mailed Nov. 2, 2023.
Notice of Allowance for U.S. Appl. No. 16/554,774 mailed Mar. 22, 2023.
Notice of Allowance for U.S. Appl. No. 17/533,306 mailed Oct. 31, 2023.
U.S. Appl. No. 14/967,308, filed Dec. 13, 2015.
U.S. Appl. No. 16/554,774, filed Aug. 29, 2019.
U.S. Appl. No. 18/212,880, filed Jun. 22, 2023.
U.S. Appl. No. 61/202,634, filed Mar. 20, 2009.
Final Office Action for U.S. Appl. No. 16/048,481 mailed Jul. 11, 2024.
Non-Final Office Action for U.S. Appl. No. 16/048,481 mailed Jan. 24, 2025.
Notice of Allowance for U.S. Appl. No. 18/212,880 mailed Jan. 29, 2025.
U.S. Appl. No. 18/876,460, filed Dec. 18, 2024.
U.S. Appl. No. 63/357,122, filed Jun. 30, 2022.
U.S. Appl. No. 63/430,030, filed Dec. 4, 2022.
Advisory Action for U.S. Appl. No. 13/257,651 mailed Nov. 30, 2018.
Advisory Action for U.S. Appl. No. 14/005,330 mailed Dec. 27, 2017.
Applicant-Initiated Interview Summary for U.S. Appl. No. 13/257,651 mailed Jan. 16, 2017.

(56) References Cited

OTHER PUBLICATIONS

Applicant-Initiated Interview Summary for U.S. Appl. No. 14/005,330 mailed Apr. 28, 2016.
Applicant-Initiated Interview Summary for U.S. Appl. No. 14/005,330 mailed Mar. 15, 2017.
Applicant-Initiated Interview Summary for U.S. Appl. No. 14/005,330 mailed Nov. 9, 2017.
Applicant-Initiated Interview Summary for U.S. Appl. No. 14/005,330 mailed Oct. 6, 2016.
Applicant-Initiated Interview Summary for U.S. Appl. No. 14/768,766 mailed Feb. 4, 2019.
Applicant-Initiated Interview Summary for U.S. Appl. No. 14/967,308 mailed Feb. 12, 2019.
Communication Pursuant to Article 94(3) EPC for European Application No. 10714484.2 mailed Feb. 21, 2017.
Communication Pursuant to Article 94(3) EPC for European Application No. 12716658.5 mailed Mar. 23, 2016.
Communication Pursuant to Article 94(3) EPC for European Application No. 12716658.5 mailed Sep. 24, 2014.
Communication Pursuant to Article 94(3) EPC for European Application No. 14764625.1 mailed Oct. 28, 2019.
Communication Relating to the Results of the Partial International Search for International Application No. PCT/IL2010/000229 mailed Nov. 8, 2010.
Communication Relating to the Results of the Partial International Search for International Application No. PCT/IL2012/050094 mailed Jul. 4, 2012.
European Search Report and Search Opinion for European Application No. 18215225.6 mailed Jan. 17, 2020.
Examiner-Initiated Interview Summary for U.S. Appl. No. 14/005,330 mailed Nov. 29, 2016.
Final Office Action for U.S. Appl. No. 13/257,651 mailed Apr. 19, 2017.
Final Office Action for U.S. Appl. No. 13/257,651 mailed Jul. 16, 2018.
Final Office Action for U.S. Appl. No. 13/257,651 mailed Mar. 16, 2015.
Final Office Action for U.S. Appl. No. 13/257,651 mailed Mar. 24, 2016.
Final Office Action for U.S. Appl. No. 14/005,330 mailed Aug. 18, 2017.
Final Office Action for U.S. Appl. No. 14/005,330 mailed Aug. 24, 2016.
Final Office Action for U.S. Appl. No. 14/768,766 mailed Apr. 2, 2021.
Final Office Action for U.S. Appl. No. 14/768,766 mailed Aug. 23, 2021.
Final Office Action for U.S. Appl. No. 14/768,766 mailed Jul. 29, 2019.
Final Office Action for U.S. Appl. No. 14/967,308 mailed Dec. 13, 2018.
International Preliminary Report on Patentability for International Application No. PCT/IL2010/000229 mailed Sep. 29, 2011.
International Preliminary Report on Patentability for International Application No. PCT/IL2012/050094 mailed Sep. 26, 2013.
International Preliminary Report on Patentability for International Application No. PCT/IL2014/050281 mailed Sep. 24, 2015.
International Search Report and Written Opinion from International Application No. PCT/IL2010/000229 mailed Jan. 18, 2011.
International Search Report and Written Opinion from International Application No. PCT/IL2012/050094 mailed Sep. 13, 2012.
International Search Report and Written Opinion from International Application No. PCT/IL2014/050281 mailed Jul. 3, 2014.
International Search Report and Written Opinion from International Application No. PCTIB2021055063 mailed Aug. 10, 2021.
Non-Final Office Action for U.S. Appl. No. 13/257,651 mailed Aug. 12, 2014.
Non-Final Office Action for U.S. Appl. No. 13/257,651 mailed Sep. 15, 2015.
Non-Final Office Action for U.S. Appl. No. 13/257,651 mailed Sep. 8, 2017.
Non-Final Office Action for U.S. Appl. No. 13/257,651 mailed Sep. 9, 2016.
Non-Final Office Action for U.S. Appl. No. 14/005,330 mailed Feb. 16, 2016.
Non-Final Office Action for U.S. Appl. No. 14/005,330 mailed Mar. 1, 2017.
Non-Final Office Action for U.S. Appl. No. 14/768,766 mailed Jul. 22, 2020.
Non-Final Office Action for U.S. Appl. No. 14/768,766 mailed Nov. 19, 2018.
Non-Final Office Action for U.S. Appl. No. 14/967,308 mailed Mar. 28, 2018.
Non-Final Office Action for U.S. Appl. No. 16/048,481 mailed Mar. 11, 2022.
Non-Final Office Action for U.S. Appl. No. 16/554,774 mailed Jun. 8, 2022.
Rectification of Obvious Mistake Under Rule 91.1. for International Application No. PCT/1L2010/000229 mailed Jul. 6, 2010.
Requisition by Examiner from the Innovation, Science and Economic Development Canada for Canadian Application No. 2,938,823 mailed Apr. 3, 2020.
Restriction Requirement for U.S. Appl. No. 13/257,651 mailed Apr. 22, 2014.
Restriction Requirement for U.S. Appl. No. 14/005,330 mailed Jul. 14, 2015.
Restriction Requirement for U.S. Appl. No. 14/768,766 mailed Apr. 20, 2018.
Restriction Requirement for U.S. Appl. No. 14/967,308 mailed Nov. 30, 2017.
Restriction Requirement for U.S. Appl. No. 16/554,774 mailed Feb. 4, 2022.
Supplementary European Search Report and the European Search Opinion for European Application No. 14764625.1 mailed Oct. 28, 2016.
U.S. Appl. No. 14/768,766, filed Aug. 19, 2015.
U.S. Appl. No. 17/533,306, filed Nov. 23, 2021.
U.S. Appl. No. 63/036,548, filed Jun. 9, 2020.
Final Office Action for U.S. Appl. No. 16/048,481 mailed Dec. 11, 2025.
Issue Notification for U.S. Appl. No. 18/212,880 mailed Apr. 30, 2025.
Non-Final Office Action for U.S. Appl. No. 16/048,481 mailed Jul. 8, 2025.
Notice of Allowance for U.S. Appl. No. 16/048,481 mailed Mar. 10, 2026.
Office Action for Japanese Application No. 2022-575788 mailed Mar. 12, 2025.

METHODS AND DEVICES FOR URETHRAL TREATMENT

CROSS-REFERENCES TO RELATED APPLICATIONS

The present application is a US national phase application of PCT Application No. PCT/IB2021/055063 to Heftman (published as WO 21/250588), filed Jun. 9, 2021, which claims priority from U.S. Provisional Patent Application No. 63/036,548 to Heftman et al., filed Jun. 9, 2020, entitled "Method and Devices for Urethral Treatment", which is incorporated herein by reference.

FIELD OF EMBODIMENTS OF THE INVENTION

The present invention, in some embodiments thereof, relates to methods and devices for treatment of intrabody lumens, and, more particularly, but not exclusively, to methods and devices for dilating and/or assisting in dilation and/or maintaining dilation of the urethra to relieve obstruction resulting, for example from benign prostatic hyperplasia (BPH).

BACKGROUND

It is common for the prostate gland to become enlarged as a man ages. As a male matures, the prostate goes through two main periods of growth, first early in puberty, and then again at later age, when the growth begins again, and continues on through life. One of the effects of this continued growth can be pressure on the urethra, the passage through which urine passes from the bladder and the penis.

The urethra is surrounded by the prostate for part of its length. Within the confines of the prostate, the urine flows through a passage having a generally triangular cross-section. As the prostate enlarges, the layer of tissue surrounding the prostate restricts the prostate from expanding outward, causing the prostate to constrict the urethral passage. The condition of an enlarged, non-cancerous prostate is called benign prostatic hyperplasia (BPH).

Though the prostate continues to grow during most of a man's life, benign prostatic hyperplasia rarely causes symptoms before age 40, but more than half of men in their sixties and as many as 90 percent in their seventies and eighties have some symptoms. BPH can make it difficult to completely empty the bladder and is associated with other urinary system problems.

SUMMARY

In some embodiments of the present invention, apparatus and methods for treatment of a urethra that is constricted due to benign prostatic hyperplasia (BPH), are provided. Typically, the apparatus includes a device having a delivery tool, which has a proximal portion and a distal portion. The distal portion of the delivery tool is configured to be advanced to a location in an area of the urethra that is to be treated due to enlargement of the prostate and consequent constriction of the area to be treated. In some embodiments the distal portion includes an operational head having an expandable element, a tissue cutter, and an implant. The expandable element e.g., a balloon, expands within the urethra such as to enlarge the urethra and dilate the constricted area. The tissue cutter is typically disposed outside of an outer surface of the expandable element and forms a cut in an inner surface of the urethra, subsequently to the expandable element having expanded in the urethra.

The implant is then released into the cut within the inner surface of the urethra and implanted in tissue of the prostate surrounding the cut in the urethra, to maintain the urethra in a dilated state. In accordance with some embodiments of the present invention, the implant comprises a shape-memory material, being shape set such that in an unconstrained configuration of the implant, the implant is substantially straight. In some embodiments, the implant is shaped to define two end sections and a middle section disposed between the two end sections, and the shape memory-material is shape set such that in an unconstrained configuration of the implant, at least the middle section is substantially straight. (In some instances, such an implant is described herein as a "quasi-straight implant".)

In accordance with some embodiments of the present invention, upon implantation of the implant in the cut formed in the urethra, the implant is constrained into a curved shape by the tissue in which the implant is implanted. Due to the tendency of the shape-memory material to return to its pre-set generally straight configuration, the implant applies radially outward pressure to the tissue. By being shape set in the generally straight configuration, the implant typically dilates the urethra more effectively than if the implant were to be shape set such as to define a less generally straight shape.

In accordance with some embodiments of the present invention, the device further includes one or more implant carrier arms extending from a shaft of the delivery tool and being disposed outside the outer surface of the expandable element. The implant carrier arms typically release the implant into the cut, subsequently to the tissue cutter forming the cut in the inner surface of the urethra. In some embodiments, one or more implant holders are coupled to the implant carrier arm and the implant is disposed between the implant carrier arm and the implant holder such that the implant is held in place during delivery of the implant. Subsequently to the tissue cutter forming the cut in the urethra, the implant holders are retracted proximally with respect to the implant carrier arms such that the implant is released by the implant carrier arms into a cut within the urethra, to maintain the urethra in a dilated state.

There is therefore provided in accordance with some embodiments of the present invention, apparatus including:

a device for treatment of a urethra that is constricted due to benign prostatic hyperplasia (BPH), the device including:

a delivery tool having a proximal portion and a distal portion, the distal portion configured to be advanced to a location in an area of the urethra that is to be treated, and the distal portion including:

an expandable element that is configured to expand within the urethra such as to enlarge the urethra in the area to be treated, the expandable element defining an outer surface;

a tissue cutter disposed outside the outer surface of the expandable element, the tissue cutter configured to form a cut in an inner surface of the urethra, subsequent to the expandable element having expanded such as to dilate the urethra; and an implant that includes a shape-memory material, and being configured to maintain the urethra in a dilated state, by being implanted within the cut in the inner surface of the urethra, the implant including two end sections and a middle section disposed between the two end sections, and the shape memory-material being shape set such that in an unconstrained configuration of the implant, the middle section is substantially straight.

In some embodiments, the implant is configured to be implanted within the cut in the urethra such that the middle section of the implant is constrained into a curved shape.

In some embodiments, a length of the middle section of the implant is at least 50% of a length of the implant.

In some embodiments, a length of the middle section of the implant is at least 60% of a length of the implant.

In some embodiments, a length of the middle section of the implant is at least 70% of a length of the implant.

In some embodiments, the implant is configured to be maintained in a spiral shape, while the implant is disposed within the delivery tool In some embodiments, the implant has a length of 40-80 mm.

In some embodiments, the implant has a thickness of 0.01-1 mm.

In some embodiments, the implant has a width of 0.5-4 mm.

In some embodiments, the implant is configured to apply pressure within the cut in the urethra of from about 25 gr to about 500 gr.

In some embodiments, the tissue cutter is configured to form the cut having a depth of 2-10 mm.

In some embodiments, the tissue cutter has a length of 3-10 mm.

In some embodiments, the tissue cutter is configured to form the cut at an angle of 90 degrees with respect to a longitudinal axis of the delivery tool.

In some embodiments, the tissue cutter is configured to form the cut at an angle other than 90 degrees with respect to a longitudinal axis of the delivery tool.

In some embodiments, the tissue cutter is configured to form the cut at an angle of from about 45 degrees to about 89 degrees with respect to a longitudinal axis of the delivery tool.

In some embodiments, the expandable element is configured to be inflated to an internal volume of 3-15 $mm^3$.

In some embodiments, the expandable element is configured to be inflated to define a diameter of 5-35 mm.

In some embodiments, the expandable element has a length of 3-100 mm.

In some embodiments, the expandable element is configured to be inflated to an internal pressure of 1-20 atm.

In some embodiments, the expandable element includes a balloon.

In some embodiments, the apparatus further includes one or more implant carrier arms extending from a shaft of the delivery tool and being disposed outside the outer surface of the expandable element.

In some embodiments, subsequently to the tissue cutter forming the cut in the inner surface of the urethra, the one or more implant carrier arms are configured to release the implant into the cut.

In some embodiments, the apparatus further includes one or more implant holders coupled to the implant carrier arms, and:

the implant is configured to be disposed between the implant carrier arm and the implant holder such that the implant is held in place by the implant carrier arm and the implant holder; and the implant holders being configured to be retracted proximally with respect to the implant carrier arms such that the implant is released by the implant carrier arms into a cut within the urethra, to thereby maintain the urethra in a dilated state.

In some embodiments, the delivery tool further includes an optical element, and the one or more implant carrier arms and the expandable element are configured so as to allow the optical element to visualize the urethra.

There is yet further provided in accordance with some embodiments of the present invention, a method for treating a urethra that is constricted due to benign prostatic hyperplasia (BPH), including:

identifying a constricted area of the urethra requiring treatment;

inserting into the urethra a delivery tool that includes an expandable element that defines an outer surface, and a tissue cutter disposed outside the outer surface of the expandable element;

using the delivery tool, delivering, to the identified constricted area of the urethra, an implant that includes a shape-memory material and has two end sections and a middle section disposed between the two end sections, the shape memory-material being shape set such that in an unconstrained configuration of the implant, the middle section is substantially straight;

expanding the urethra by expanding the expandable element in the identified constricted area of the urethra;

subsequently, forming a cut in an inner surface of the urethra using the tissue cutter; and releasing the implant into the cut to maintain the urethra in a dilated state.

In some embodiments, delivering the implant to the identified constricted area of the urethra includes delivering the implant while the implant is compressed into a spiral configuration.

In some embodiments, releasing the implant into the cut to maintain the urethra in a dilated state, includes releasing the implant into the cut while the middle section of the implant is constrained into a curved shape.

In some embodiments, the delivery tool further includes one or more implant carrier arms extending from a shaft of the delivery tool and being disposed outside the outer surface of the expandable element and delivering the implant to the identified constricted area of the urethra includes delivering the implant while the implant is in a removably coupled state with respect to the one or more implant carrier arms.

In some embodiments, releasing the implant into the cut includes releasing the implant from the one or more implant carrier arms.

In some embodiments, the delivery tool further includes one or more implant holders coupled to the implant carrier arms and delivering the implant to the identified constricted area of the urethra includes delivering the implant while the implant is held in place with respect to the one or more implant carrier arms by being disposed between the one or more implant carrier arms and the one or more implant holders.

In some embodiments, releasing the implant into the cut includes retracting one of the one or more implant holders proximally with respect to one of the one or more implant carrier arms.

In some embodiments, releasing the implant includes releasing a distal portion of the implant prior to expanding the expandable element and releasing a proximal portion of the implant subsequently to expanding the expandable element.

There is still further provided in accordance with some embodiments of the present invention, apparatus including:

a device for treatment of a urethra that is constricted due to benign prostatic hyperplasia (BPH), the device including:

a delivery tool having a proximal portion and a distal portion, the distal portion configured to be advanced to a location in an area of the urethra that is to be treated and the distal end including:

one or more implant carrier arms extending from a shaft of the delivery tool; and one or more implant holders coupled to the one or more implant carrier arms; and an implant configured to be disposed between the one or more implant carrier arms and the one or more implant holders such that the implant is held in place by the one or more implant carrier arms and the one or more implant holders, the one or more implant holders being configured to be retracted proximally with respect to the one or more implant carrier arms such that the implant is released from the one or more implant carrier arms into a cut within the urethra, to thereby maintain the urethra in a dilated state.

In some embodiments, the implant is held in a spiral configuration between the one or more implant carrier arms and the one or more implant holders.

In some embodiments, the one or more implant holders are configured to be retracted proximally to release a distal end of the implant prior to releasing a proximal end of the implant.

In some embodiments, the apparatus further includes a tissue cutter configured to form a cut in an inner surface of the urethra, and the implant is configured to be released into the cut.

In some embodiments, the apparatus further includes an optical element, and the one or more implant carrier arms and the expandable element are configured so as to allow the optical element to visualize the urethra.

In some embodiments, the apparatus further includes an expandable element that is configured to expand within the urethra such as to expand the urethra in the area to be treated.

In some embodiments, one of the one or more implant holders is configured to be retracted proximally to release a distal end of the implant prior to expanding of the expandable element, and a proximal end of the implant is configured to be released subsequently to expanding of the expandable element.

There is still further provided in accordance with some embodiments of the present invention, a method for treating a urethra that is constricted due to benign prostatic hyperplasia (BPH), including:

identifying a constricted area of the urethra requiring treatment;

inserting into the urethra a longitudinal delivery tool that includes:

an expandable element that defines an outer surface, a tissue cutter disposed outside the outer surface of the expandable element, one or more implant carrier arms extending from a shaft of the delivery tool, and one or more implant holders coupled to the implant carrier arms, and an implant disposed between the one or more implant carrier arms and the one or more implant holders such that the implant is held in place by the one or more implant carrier arms and the one or more implant holders;

delivering the implant for deployment at the identified constricted area of the urethra;

releasing a distal portion of the implant by retracting one of the one or more implant holders proximally with respect to the implant carrier arm;

expanding the urethra using the expandable element at the identified constricted area of the urethra;

forming a cut in the inner surface of the urethra; and releasing a proximal portion of the implant by retracting one of the one or more implant holders proximally with respect to one of one or more implant carrier arms, thereby releasing the implant into the cut.

In some embodiments, delivering the implant for deployment at the identified constricted area of the urethra includes delivering the implant while the implant is held in a spiral configuration between the one or more implant carrier arms and the one or more implant holders.

In some embodiments, releasing the distal portion of the implant includes releasing the distal portion of the implant prior to expanding the expandable element and releasing the proximal portion of the implant includes releasing the proximal portion subsequently to expanding the expandable element.

There is still further provided in accordance with some embodiments of the present invention, an operational head for implantation system for dilating a urethra at least partially obstructed by an enlarged prostate including:

a. a quasi-straight implant;

b. at least two arms connected to a shaft and including implant holders to which the quasi-straight implant is removably attached;

c. an expandable body surrounded by the at least two arms and the quasi-straight implant is wrapped around the expandable element;

d. an optical element extending from the handle inside the shaft;

the at least two arms and the expandable element are configured so as to allow the optical element to visualize the urethra.

In some embodiments, the implant is configured to be at least partially embedded through the wall of an enlarged portion of the prostate surrounding a constricted portion of the urethra.

In some embodiments, the quasi-straight implant includes pad-like endings at each end.

In some embodiments, the quasi-straight implant includes one or more protrusions located at each end configured to stabilize the quasi-straight implant once implanted inside the cut.

In some embodiments, the quasi-straight implant includes a length of from about 40 mm to about 80 mm.

In some embodiments, the quasi-straight implant includes a thickness of from about 0.01 mm to about 1 mm.

In some embodiments, the quasi-straight implant includes a width of from about 0.5 mm to about 4 mm.

In some embodiments, the quasi-straight implant includes a middle straight section and two slightly curved end sections.

In some embodiments, the quasi-straight implant is configured to apply forces on the wall of from about 25 gr to about 500 gr.

In some embodiments, the at least two arms include a sleeve that partially covers the arms.

In some embodiments, the operational head include three arms.

In some embodiments, the at least two arms are configured to perform inward-outward movements, which accompany the inflation deflation if the expandable body.

In some embodiments, a relationship of width/thickness of the at least two arms provide the at least two arms with the necessary strength to resist bending due to rotational movements of the shaft.

In some embodiments, the implant holders are covered by the sleeve.

In some embodiments, the implant holders are configured to move proximally and distally in relation to the at least two arms.

In some embodiments, the operational head further includes a tissue cutter extending from a handle to the operational head and configured to perform a cut in the wall, the cut being the place where the implant is to be at least partially embedded.

In some embodiments, the cutter includes an L-shape operating configuration.

In some embodiments, the cutter is configured to cut by rotating the shaft.

In some embodiments, the cutter is configured to perform a cut having a depth of from about 2 mm to about 10 mm.

In some embodiments, the tissue cutter includes a length of from about 3 mm to about 10 mm.

In some embodiments, the cutter is connected to an electrical or electromechanical energy.

In some embodiments, the cutter includes a distal end including a T-like shape.

In some embodiments, the cutter includes a distal end including a rounded shape.

In some embodiments, the cutter is configured to deployed and/or inserted from the shaft by a user.

In some embodiments, the cutter performs a cut at an angle of 90 degrees in relation to the longitudinal axis of the device.

In some embodiments, the cutter performs a cut at an angle other than 90 degrees in relation to the longitudinal axis of the device.

In some embodiments, the cutter performs a cut at an angle of from about 45 degrees to about 89 degrees in relation to the longitudinal axis of the device.

In some embodiments, the expandable body includes an internal volume of from about 3 $mm^3$ to about 15 $mm^3$.

In some embodiments, the expandable body includes a diameter of from about 5 mm to about 35 mm.

In some embodiments, the expandable body includes a length of from about 3 mm to about 100 mm.

In some embodiments, the expandable body can be inflated to an internal pressure of from about 1 atm to about 20 atm.

In some embodiments, the expandable body includes a balloon.

In some embodiments, the expandable body is a balloon.

In some embodiments, the expandable body is made of elastic materials.

In some embodiments, the expandable body is in communication with a tube extending from the handle, the tube configured to transport the material that causes the expandable body to be inflated/deflated.

In some embodiments, the expandable body is enclosed in a jacket configured to protect the expandable body.

In some embodiments, the jacket limits the inflation of the expandable body.

In some embodiments, a distal end of the optical element is located before a proximal end of the operational head.

In some embodiments, the distal end of the optical element is located at about ±2 mm of a distal end of the shaft.

In some embodiments, the optical element includes a field of view of from about 0 degrees to about ±120 degrees.

In some embodiments, the handle includes one or more controllers configured to actuate the at least two motors.

In some embodiments, the handle includes one or more controllers configured to synchronize the actuation of the at least two motors.

In some embodiments, the at least two motors are configured to operate at a velocity of from about 1 RPM to about 1000 RPM.

In some embodiments, the at least two motors are configured to provide a force of from about 1 Kg to about 5 Kg.

In some embodiments, the at least two motors are configured to provide linear movements and/or rotational movements to one or more of the elongated body and the shaft.

In some embodiments, the rotational movement includes a velocity of from about 1 rotation per second to about 1 rotation per 3 seconds.

In some embodiments, the rotational movement includes a rotational force (torque) of from about 50 Nmm to about 300 Nmm.

In some embodiments, the linear movement includes a velocity of from about 1 mm/s to about 10 mm/s.

In some embodiments, the elongated body includes an internal diameter of from about 3 mm to about 20 mm.

In some embodiments, the shaft includes an internal diameter of from about 3 mm to about 20 mm.

In some embodiments, a device including the operational head includes an internal guiding element including one or more channels configured to provide dedicated channels to elements extending from the handle to the operational head.

In some embodiments, a system including the operational head includes an outer sheath configured to allow washing during the implantation procedure.

There is still further provided in accordance with some embodiments of the present invention, an implantation system for dilating a urethra at least partially obstructed by an enlarged prostate including:

a. a quasi-straight implant configured to be at least partially embedded through the wall of an enlarged portion of the prostate surrounding a constricted portion of the urethra;
b. a handle including a first motor configured to actuate linear movements, a second motor configured to actuate rotational movements and a controller configured to synchronize actuation between the first motor and the second motor;
c. an elongated body extending from the handle and connected to the first motor and configured to house an internal shaft including an operational head;
d. a shaft extending from the handle and connected to the second motor at its proximal end and including an operational head at its distal end.

In some embodiments, the operational head includes at least two arms connected to the shaft and including implant holders to which the quasi-straight implant is removably attached, the implant holders connected to the elongated body.

In some embodiments, the operational head includes a tissue cutter extending from the handle to the operational head and configured to perform a cut in the wall, the tissue cutter configured to rotate with the shaft.

In some embodiments, the operational head includes an expandable body surrounded by at least two arms and the quasi-straight implant is wrapped around the expandable element.

In some embodiments, the system further including an optical element extending from the handle inside the shaft and configured to allow a user to visualize the location of the constricted portion of the urethra.

In some embodiments, the implant is configured to be at least partially embedded through the wall of an enlarged portion of the prostate surrounding a constricted portion of the urethra.

There is still further provided in accordance with some embodiments of the present invention, a method for dilating a urethra using an implant and a delivery system including an expandable body, the method including:

a. releasing a distal end of the implant
b. expanding the expandable body thereby expanding the urethra and;
c. releasing a proximal end of the implant.

In some embodiments, the method further includes loading the implant in a helix configuration on the delivery system.

In some embodiments, the method further includes inserting the delivery system into the urethra.

In some embodiments, the method further includes exposing a tissue cutter and rotating the delivery system so as to perform a cut in a wall of the urethra.

In some embodiments, the releasing the proximal end causes the implant to implanting the implant in the cut on the wall of the urethra.

In some embodiments, the implant is formed of a material, which expands outwardly in the cut of the wall of the urethra during and/or after implantation.

In some embodiments, the expanding the expandable body causes radially expanding the implant from the helix configuration to a C-shape arc configuration.

In some embodiments, the implant provides clearance between the enlarged prostate and a lumen of the urethra, and prevents recompression of the urethra due to further enlargement of the prostate.

In some embodiments, the method includes selecting the implant length and position to not interfere with an inner bladder valve.

There is still further provided in accordance with some embodiments of the present invention, an implantation system for dilating a urethra at least partially obstructed by an enlarged prostate including:

a. a quasi-straight implant configured to be at least partially embedded through the wall of an enlarged portion of the prostate surrounding a constricted portion of the urethra;
b. a delivery device for the quasi-straight implant including:
    i. a handle including at least one operational button and at least two motors;
    ii. an elongated body connected to the handle and configured to house an internal shaft including an operational head;
    iii. a shaft extending from the handle and interconnected to the at least two motors at its proximal end and including an operational head at its distal end;
    iv. an operational head including:
        A. at least two arms connected to the shaft and including implant holders to which the quasi-straight implant is removably attached;
        B. a tissue cutter extending from the handle to the operational head and configured to perform a cut in the wall, the cut being the place where the implant is to be at least partially embedded; and
        C. an expandable body surrounded by the at least two arms and the quasi-straight implant is wrapped around the expandable element;
c. an optical element extending from the handle inside the shaft and configured to allow a user to visualize the location of the constricted portion of the urethra.

There is still further provided in accordance with some embodiments of the present invention, an operational head for implantation system for dilating a urethra at least partially obstructed by an enlarged prostate including:

a. a quasi-straight implant configured to be at least partially embedded through the wall of an enlarged portion of the prostate surrounding a constricted portion of the urethra;
b. at least two arms connected to a shaft and including implant holders to which the quasi-straight implant is removably attached;
c. a tissue cutter extending from a handle to the operational head and configured to perform a cut in the wall, the cut being the place where the implant is to be at least partially embedded; and
d. an expandable body surrounded by the at least two arms and the quasi-straight implant is wrapped around the expandable element;
e. an optical element extending from the handle inside the shaft and configured to allow a user to visualize the location of the constricted portion of the urethra.

There is still further provided in accordance with some embodiments of the present invention, an operational head for implantation system for dilating a urethra at least partially obstructed by an enlarged prostate including:

a. a quasi-straight implant;
b. at least two arms connected to a shaft and including implant holders to which the quasi-straight implant is removably attached;
c. an expandable body surrounded by the at least two arms and the quasi-straight implant is wrapped around the expandable element;
d. an optical element extending from the handle inside the shaft and configured to allow a user to visualize the location of the constricted portion of the urethra.

There is still further provided in accordance with some embodiments of the present invention, an operational head for implantation system for dilating a urethra at least partially obstructed by an enlarged prostate including:

a. a quasi-straight implant;
b. at least two arms connected to a shaft and each arm including at least two implant holders to which the quasi-straight implant is removably attached;

the implant holders are configured to release the quasi-straight implant in a sequential manner so as to allow a controllable deployment of aid quasi-straight implant.

There is still further provided in accordance with some embodiments of the present invention, an implant for dilating a urethra at least partially obstructed by an enlarged prostate including:

a. a quasi-straight body;
b. pad-like endings at each end; and
c. one or more protrusions located at each end configured to stabilize the implant once implanted.

The present invention will be more fully understood from the following detailed description of embodiments thereof, taken together with the drawings, in which:

DETAILED DESCRIPTION

Figure 1A:
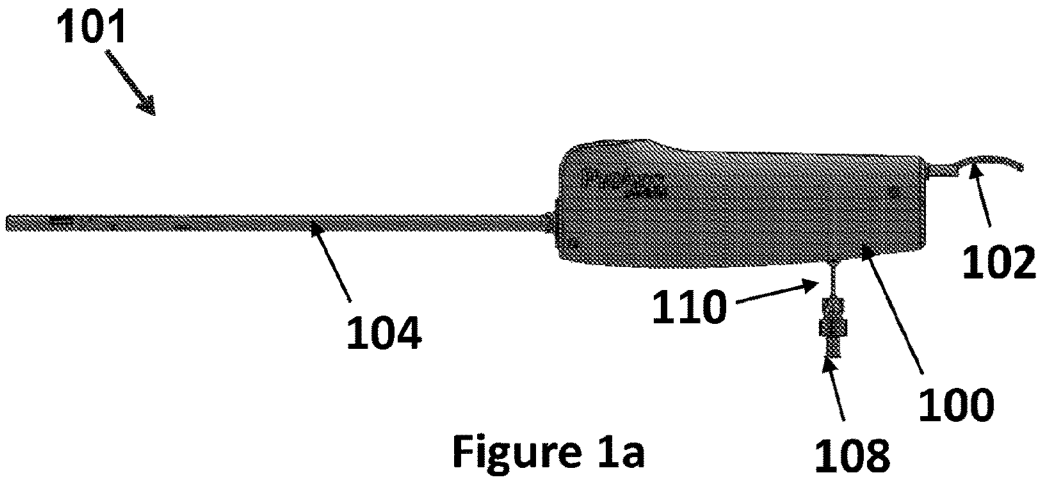
FIGS. 1*a* and 1*b* are schematic illustrations of generic views of a device for dilating a urethra of a subject at least partially obstructed by an enlarged prostate, according to some embodiments of the invention.

The present invention, in some embodiments thereof, relates to methods and devices for treatment of intrabody lumens, and, more particularly, but not exclusively, to methods and devices for dilating and/or assisting in dilation and/or maintaining dilation of the urethra to relieve obstruction resulting, for example, from benign prostatic hyperplasia (BPH). A broad aspect of some embodiments of the invention relates to increasing reliability in urethral implantation procedures by improving the device and the implant by means of improved engineering, interface and automation.

Overview

Some embodiments of the invention relate to synchronizing actions to implant an implant in a cut made in the walls of the urethra. In some embodiments, one or more actions are performed by a device for dilating and/or assisting in dilation and/or maintaining dilation of the urethra to relieve obstruction resulting, for example, from benign prostatic hyperplasia (BPH). In some embodiments, one or more actions are performed by translating directional movements at a handle of the device to implantation actions at a distal end of the device. In some embodiments, directional movements are one or more of linear movements, or rotational movements, and any combination thereof. In some embodiments, movements at the handle are actuated by one or more motors controlled and/or synchronized by one or more controllers. In some embodiments, synchronization of actions includes one or more of synchronization of rotational movements with linear movement to correctly activate different parts of the device. In some embodiments, one or more actions are performed automatically one after another to allow repeatability of the implantation method and potentially reducing human error during implantation. In some embodiments, after each automated action(s) a visual and/or sonic alarm informs the user that the actions are finished.

In some embodiments, the device comprises a cutter that is configured to make the cut in the walls of the urethra and in tissue of the prostate in order to create an area shaped and sized to accommodate the implant. In some embodiments, the cut is created by the cutter such that the cut is wider deeper in the tissue compared to the cut at the surface of the tissue.

Some embodiments of the invention relate to an implant configured to be implanted inside the cut formed by the cutter in the walls of the urethra. Typically, the implant is configured to be at least partially embedded through the wall of an enlarged portion of the prostate surrounding a constricted portion of the urethra. In some embodiments, the implant is a thin implant configured to be implanted deeper in tissue when compared to less thin implants.

In some embodiments, the implant is made of a shape-memory alloy, such as nitinol. Typically, the shape-memory alloy of the implant is shape set such that the implant assumes a generally straight shape along more than 50 percent (e.g., more than 60 percent or more than 70 percent) of its length when in an unconstrained state (i.e., in the absence of any forces being applied to the implant). (In some instances, such an implant is described herein as a "quasi-straight implant".) Typically, upon implantation of the implant in the cut formed in the urethra, the implant is constrained into a curved shape by the tissue in which the implant is implanted. Due to the tendency of the shape-memory alloy to return to its pre-set generally straight configuration, the implant applies radially outward pressure to the tissue. By being shape set in the above-described manner, the implant typically dilates the urethra more effectively than if the implant were to be shape set such as to define a less generally straight shape.

In some embodiments, the implant comprises pads at the end of the implant configured to provide stability to the implant once implanted in the implantation site inside the cut. In some embodiments, the implant comprises one or more protrusions configured to stabilize the implant once implanted in the implantation site inside the cut, the protrusions shaped to be blunt so they will not damage the tissue.

Some embodiments of the invention relate to an implantation device configured to implant at least one implant in the urethra wall comprising at least one optical element, which allows the user to perform the implantation procedure under direct visualization of the desired implantation site and/or direct visualization of the implantation procedure itself and/or direct visualization of the correct implant implantation. In some embodiments, visualization of the implantation site is performed before inflating the inflatable body. In some embodiments, the optical element has a field of view of from about 0 degrees (meaning looking forward) to about ±90 degrees. In some embodiments, the desired implantation site is selected not to interfere with an inner bladder valve. In some embodiments, the desired implantation site is selected as the site which the urethra is most blocked. In some embodiments, visualization of the implantation procedure comprises one or more of visualizing the expansion of the urethra, visualizing the cutting of the wall of the urethra, visualizing the correct deployment of the implant, optionally inside the cut.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In the following disclosure the term "distal" refers to the general direction farther from a user (e.g., a physician), while the term "proximal" refers to the general direction closer to the user; for example, something located distally may be in the body (e.g., towards the bladder), and proximal may be, for example, outside the body or towards a handle.

Exemplary Generic View

Figure 1B:
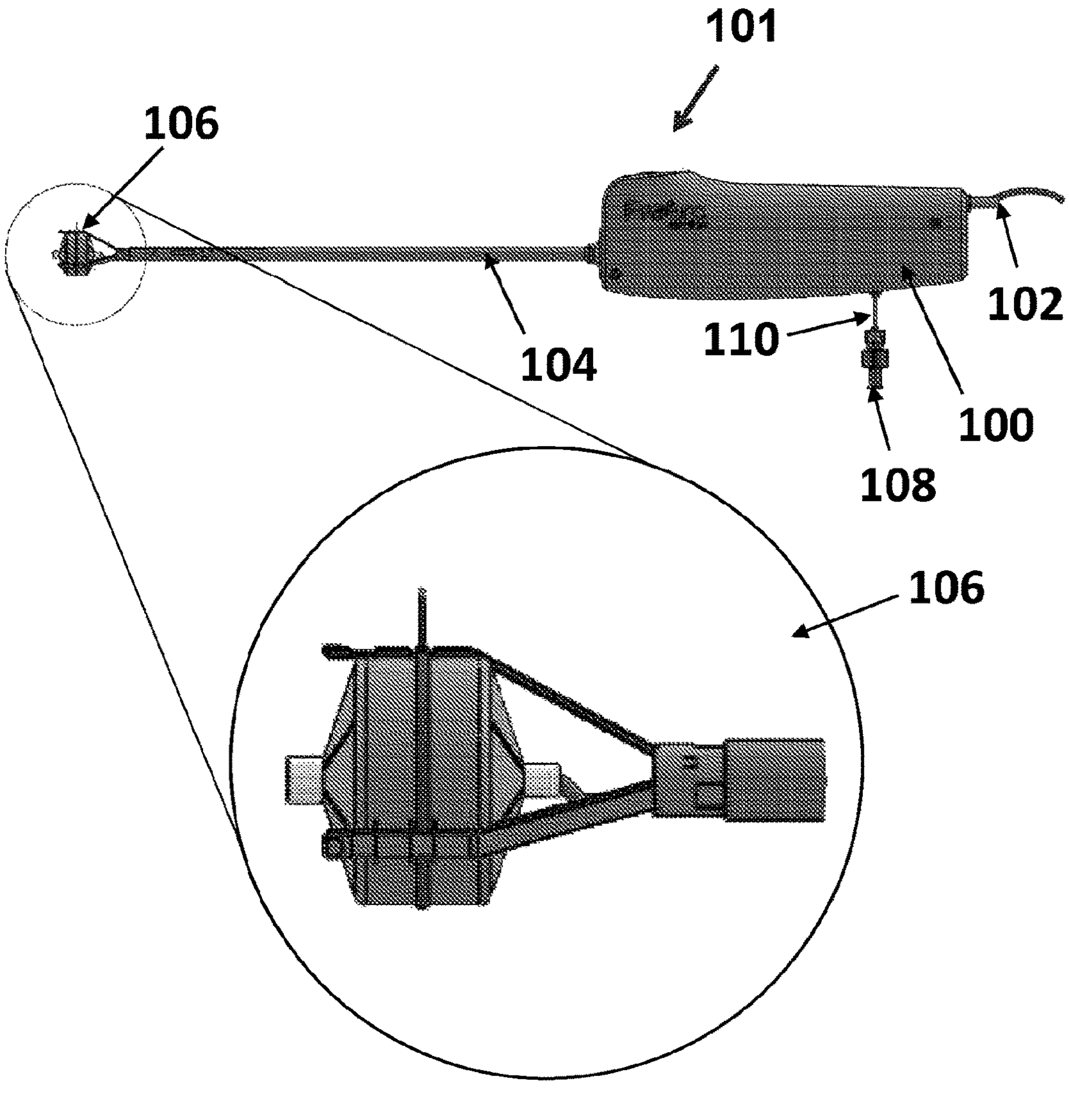

Referring now to the drawings, FIGS. 1*a* and 1*b* illustrates schematic generic views of the device for dilating a urethra of a subject at least partially obstructed by an enlarged prostate, according to some embodiments of the invention. As shown, in some embodiments, the device comprises a delivery tool 101 having a proximal portion and a distal portion, the distal portion configured to be advanced to a location in an area of the urethra. In some embodiments, the device comprises a handle 100 configured to be held by a user. In some embodiments, the handle 100 is optionally connected to a power source (not shown) via a cable 102. In some embodiments, the handle 100 optionally comprises a power source included within. In some embodiments, the delivery tool further comprises an elongated body 104 connected to the handle 100. In some embodiments, the device further comprises an operational head 106, as shown for example in FIG. 1*b*, which is shown in an expanded configuration. In some embodiments, the device comprises an inlet/outlet 108, connected to a tube 110 and configured to allow insertion and removal of fluids from the device, for example: air, water and/or saline.

Exemplary Elongated Body

Figure 2:
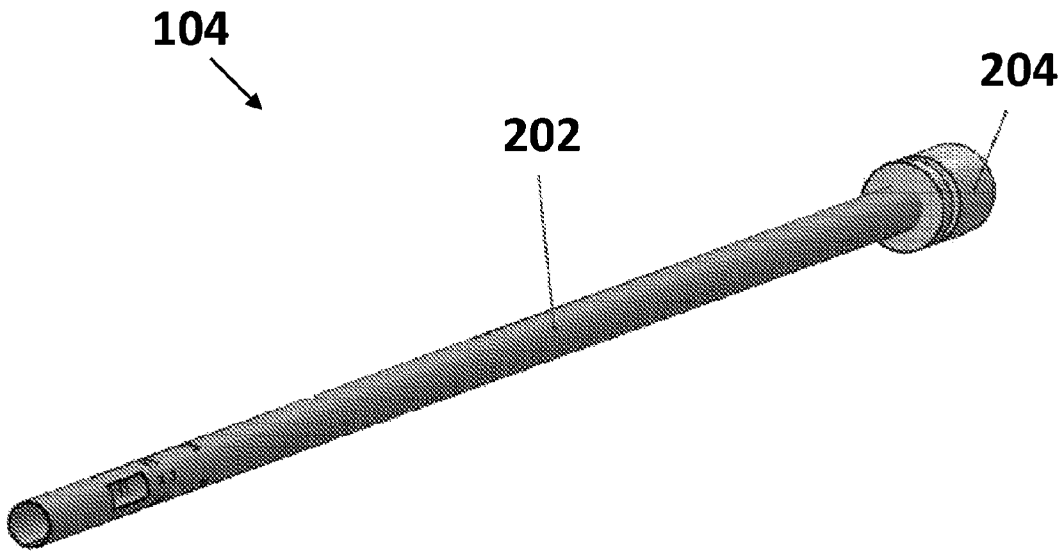
FIG. 2 is a schematic illustration of a view of an exemplary elongated body of the device for dilating a urethra of a subject at least partially obstructed by an enlarged prostate, according to some embodiments of the invention.

Referring now to FIG. 2, showing a schematic view of an exemplary elongated body 104, according to some embodiments of the invention. In some embodiments, the elongated body 104 comprises a tube 202 comprising a lumen sized and shaped to fit over an internal operational element 300 (shown in FIG. 3), thereby providing a working channel for the internal operational element 300. In some embodiments, elongated body 104 comprises a connector 204 at the proximal end configured to connect between the elongated body 104 and the handle 100 (shown in FIGS. 1*a* and 1*b*). In some embodiments, the internal diameter of the elongated body 104 is from about 3 mm to about 20 mm, optionally between 5 mm and 15 mm, optionally between 6 mm and 10 mm, for example, 5 mm, 6 mm, 7 mm, 8 mm, 10 mm or 15 mm. In some embodiments, the diameter of the elongated body 104 is calculated using the French catheter scale. In some embodiments, the diameter of the elongated body 104 is from about 5 Fr to about 50 Fr, optionally from about 10 Fr to about 30 Fr, optionally from about 15 Fr to about 25 Fr, for example 25 Fr, 20 Fr, 15 Fr or 10 Fr. In some embodiments, the elongated body 104 is made of, for example, metal or plastics, for example PEEK, PA, PEVAX, PTFE and/or FEP.

Exemplary Internal Operational Element 300

Figure 3:
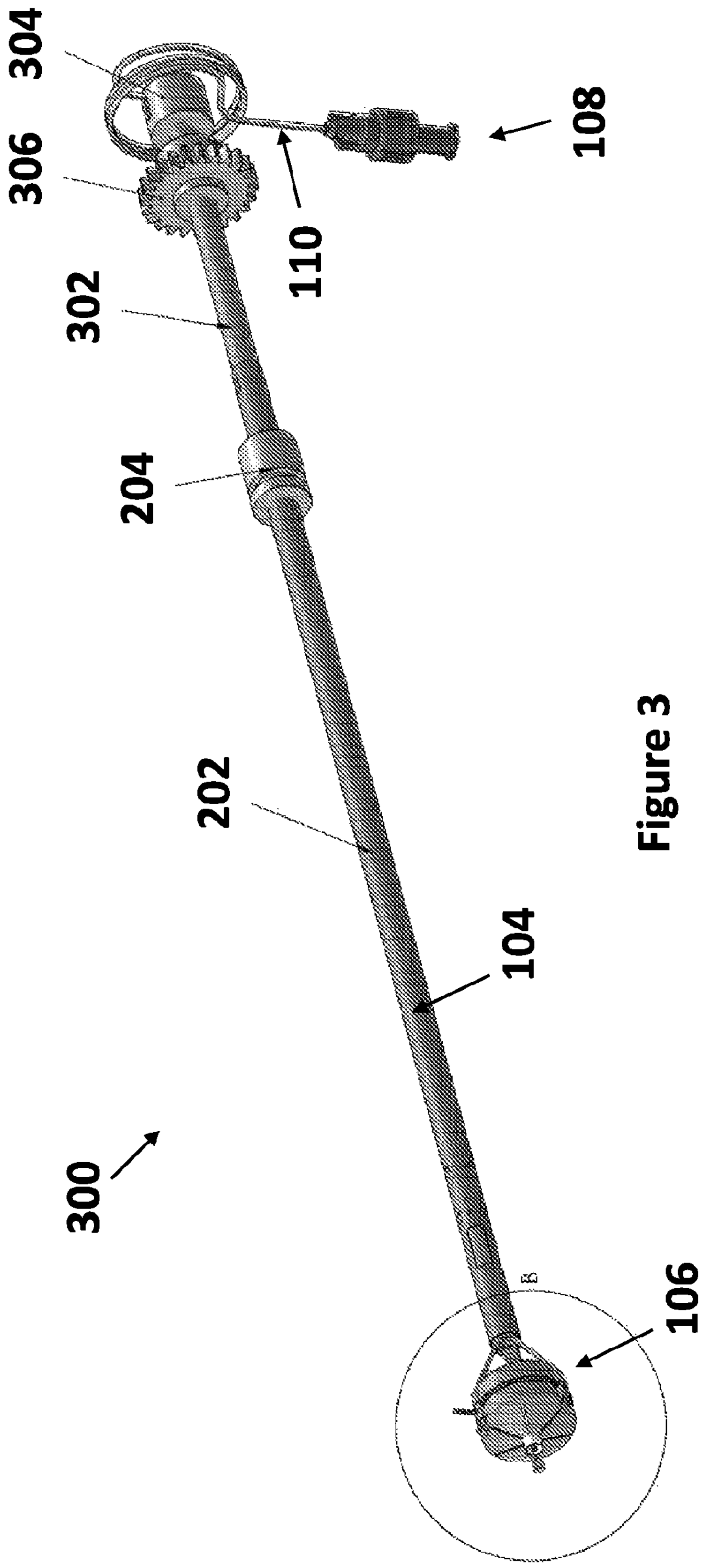
FIG. 3 is a schematic illustration of an exemplary embodiment of an internal operational element, according to some embodiments of the invention.

Referring now to FIG. 3, showing an exemplary embodiment of the internal operational element 300, according to some embodiments of the invention. In FIG. 3, the elongated body 104 is also shown to provide reference. In some embodiments, the internal operational element 300 comprises a shaft 302 sized and shaped to be inserted inside the elongated body 104.

In some embodiments, at the proximal end of the internal operational element 300 there is a connector 304 configured to connect between the internal operational element 300 and the handle 100. In some embodiments, the internal operational element 300 comprises a first gear 306 configured to interconnect between at least one motor 1104 (shown in FIGS. 11*a-b*) located at the handle and the operational head 106, thereby providing an actuation mechanism for the operational head 106 (other gears and motors are disclosed below in the "Exemplary handle and mechanisms therein" section and in FIGS. 10 and 11*a-b*). In some embodiments, the internal diameter of the shaft 302 is from about 3 mm to about 20 mm, optionally between 5 mm and 15 mm, optionally between 6 mm and 10 mm, for example, 5 mm, 6 mm, 7 mm, 8 mm, 10 mm or 15 mm. In some embodiments, the diameter of the shaft 302 is calculated using the French catheter scale. In some embodiments, the diameter of the shaft 302 is from about 5 Fr to about 50 Fr, optionally from about 10 Fr to about 30 Fr, optionally from about 15 Fr to about 25 Fr, for example 25 Fr, 20 Fr, 15 Fr or 10 Fr. In some embodiments, the shaft 302 is made of, for example, metal or plastics, for example PEEK, PA, PEVAX, PTFE and/or FEP.

Exemplary Operational Head

Figure 4A:
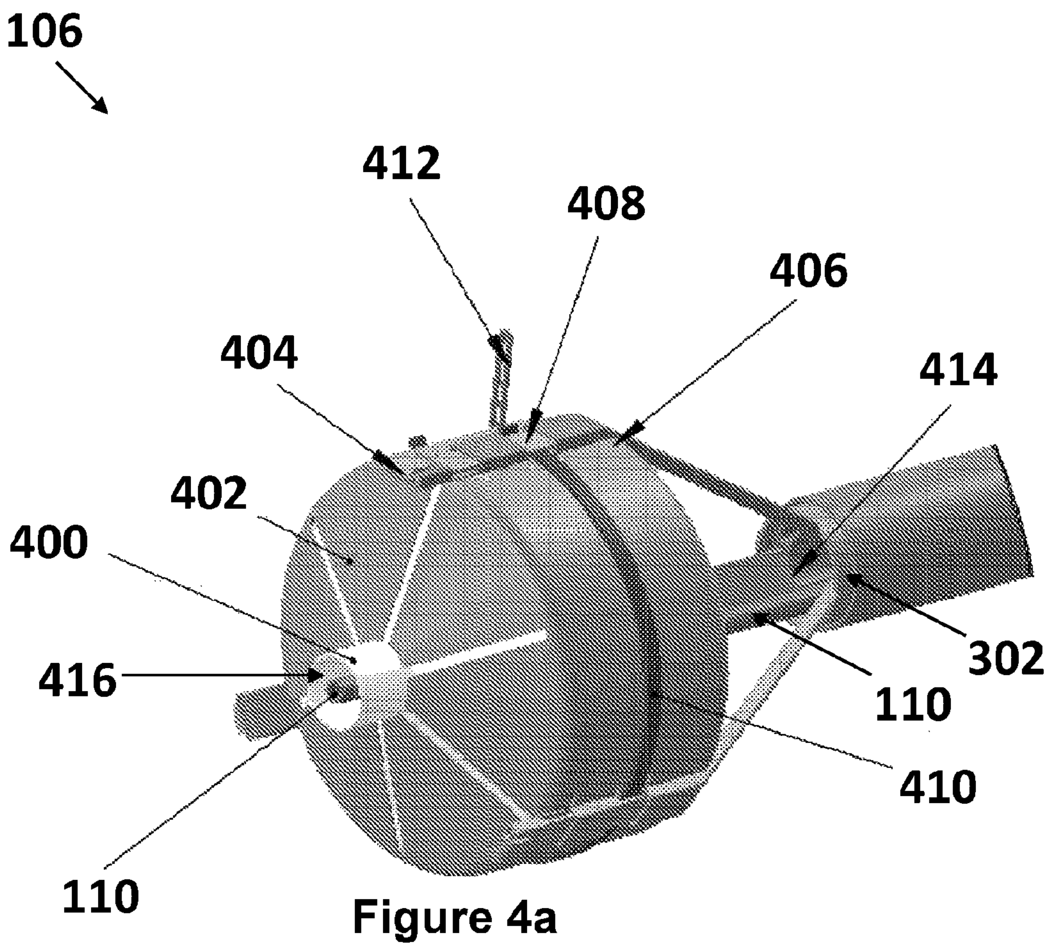
FIGS. 4*a* and 4*b* is a schematic illustration of an exemplary embodiment of an operational head in an inflated configuration, according to some embodiments of the invention.
Figure 4B:
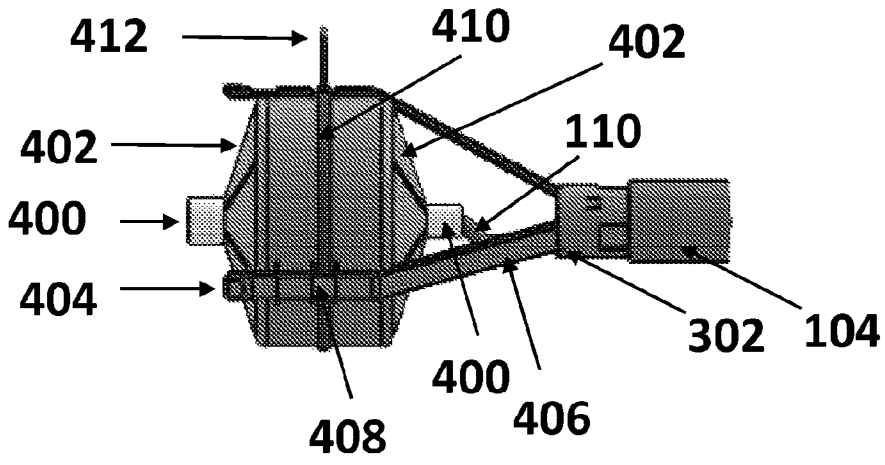

Referring now to FIGS. 4*a* and 4*b*, showing an exemplary embodiment of an operational head 106 in an expanded configuration, according to some embodiments of the invention. In some embodiments, the operational head 106 comprises a plurality of elements configured to ensure the release of an implant at the chosen location. In some embodiments, the operational head 106 comprises an expandable body 400 (also referred to herein as an "expandable element"), one or more implant carrier arms 404 connected to the shaft 302 and comprising implant holding/release mechanisms, a tissue cutter 412, an implant 410 and an internal guiding element 414.

Exemplary Expandable Body 400 and Jacket 402

Reference is still made to FIGS. 4*a* and 4*b*. In some embodiments, the operational head 106 comprises an expandable body 400 configured to be expanded and or retracted (inflated and/or deflated in case of a balloon) as chosen by the user. In some embodiments, the expandable body 400 is made of one or more materials, for example: PET, nylon, silicon, latex, polyurethane, Pebax®. In some embodiments, the expandable body is made of super-elastic materials, for example nitinol. In some embodiments, the expandable body comprises an internal volume of from about 5 $mm^3$ to about 10 $mm^3$. Optionally from about 3 $mm^3$ to about 15 $mm^3$. Optionally from about 10 $mm^3$ to about 30 $mm^3$. In some embodiments, the diameter of the expandable body is from about 10 mm to about 20 mm. Optionally from about 5 mm to about 35 mm. Optionally from about 3 mm to about 50 mm. In some embodiments, the length of the expandable body is from about 5 mm to about 80 mm. Optionally from about 3 mm to about 100 mm. Optionally from about 20 mm to about 150 mm. In some embodiments, the expandable body 400 comprises a balloon. In some embodiments, the expandable body 400 is a balloon. In some embodiments, the expandable body can be inflated to an internal pressure of from about 1 atm to about 20 atm. Optionally from about 0.5 atm to about 30 atm. Optionally from about 5 atm to about 50 atm. In some embodiments, the expandable body 400 is in communication with the tube inlet/outlet 108. In some embodiments, the expandable body 400 comprises a jacket 402 configured to enclose the expandable body 400. In some embodiments, the jacket 402 is made of non-elastic materials, for example: PET and/or PA. In some embodiments, the jacket 402 provides the expandable body 400 with protection against damage and/or with a limit to the quantity of inflation that the expandable body 400 can be inflated. FIGS. 4*a* and 4*b* also shows the distal end of the tube 110, which is connected to the expandable body 400.

Figure 5A:
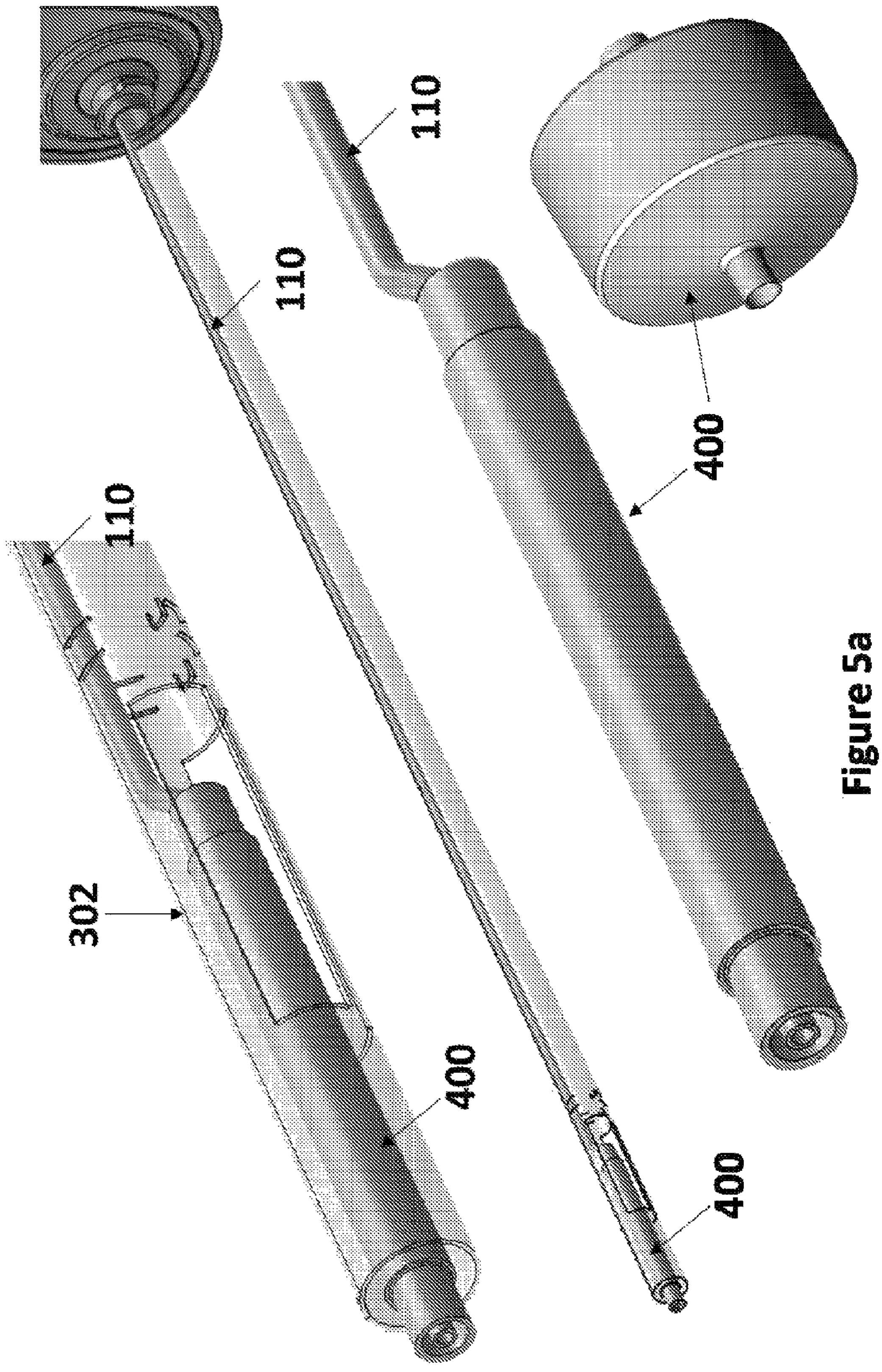
FIG. 5*a* is a schematic illustration of an exemplary expandable body, according to some embodiments of the invention.

Referring now to FIG. 5*a*, showing a schematic representation of an exemplary expandable body 400, according to some embodiments of the invention. FIG. 5*a* shows the expandable body 400 in the deflated configuration connected to the tube. Also shown is the complex expandable body 400/tube 110 with inside the shaft 302. Also shown in FIG. 5*a* is a schematic representation of the expandable body 400 in an inflated configuration. In some embodiments, the expandable body is manually inflated/deflated by the user. In some embodiments, the expandable body is automatically inflated/deflated by the device/controller.

Figure 5B:
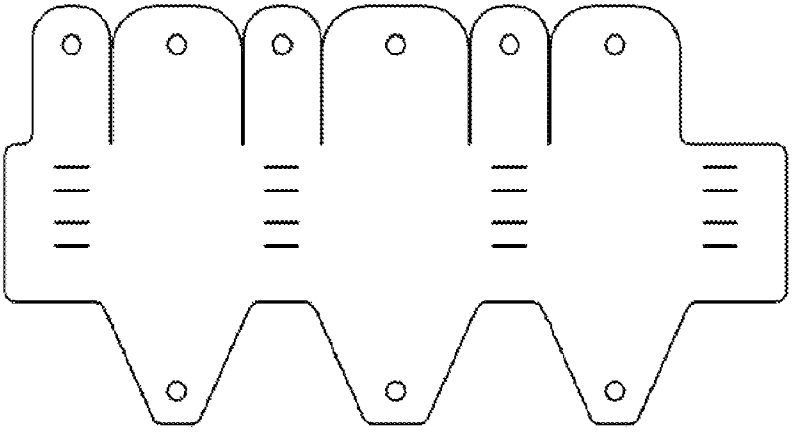
FIG. 5*b* is a schematic illustration of an exemplary jacket in an open configuration before it is mounted on an expandable body, according to some embodiments of the invention.
Figure 5C:
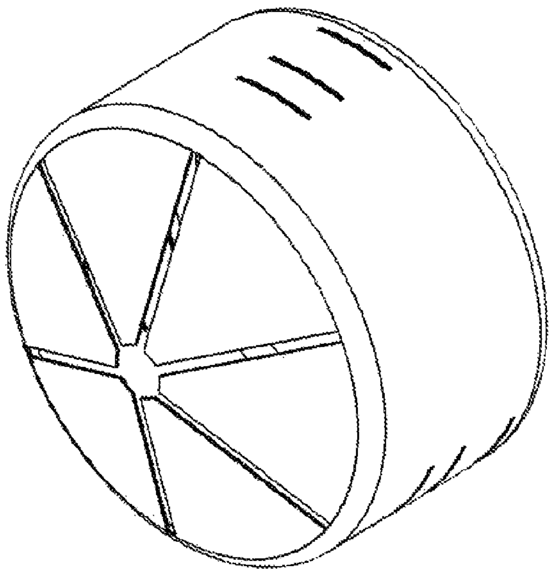
FIG. 5*c* is a schematic illustration of an exemplary jacket in a close configuration after it is mounted on an expandable body, according to some embodiments of the invention.

Referring now to FIGS. 5*b* and 5*c*: FIG. 5*b* shows an exemplary jacket in an open configuration before it is mounted on the expandable body. FIG. 5*c* shows an exemplary jacket alone as it would look like once mounted on the expandable body.

Exemplary Arms 404

Referring back to FIGS. 4*a* and 4*b*, in some embodiments, the operational head 106 further comprises one or more arms 404 connected to the shaft 302. In some embodiments, the arms 404 are flexible arms. In some embodiments, the arms 404 are made of stainless steel or any other suitable metal. In some embodiments, there can be one arm, optionally two arms, optionally three arms, optionally four arms, optionally more. In some embodiments, a potential advantage of having three arms 404 is that it provides a good relationship between functionality and stability. In some embodiments, each arm 404 is covered by a sleeve 406. In some embodiments, the sleeve 406 does not cover the entire length of the arm 404. In some embodiments, the operational head 106 further comprises a movable implant holder 408 located between the arm 404 and the sleeve 406. In some embodiments, the movable implant holder 408 is configured to hold the implant 410 in place.

In some embodiments, the order of the components is as follows, from internal to external: the expandable body 400 covered by the jacket 402. The lower part of the sleeve 406 in contact with the jacket 402, optionally attached to the jacket 402. Inside the sleeve 406, there is the arm 404. On top of the arm 404 the implant 410 and on top on the implant 410 the movable implant holder 408. In some embodiments, the implant 410 is held between the arm 404 and the movable implant holder 408, which are held together by the sleeve 406. Then, most external, the upper part of the sleeve 406.

In some embodiments, the arms 404 are configured to perform inward-outward movements in relation to the longitudinal axis of the device. In some embodiments, the inward-outward movements accompany the inflation/deflation of the expandable body. In some embodiments, the inward-outward movements occur due to the inflation/deflation of the expandable body. In some embodiments, the arms 404 are configured to resist rotational movements in relation to the longitudinal axis of the device, when shaft 302 is rotated. In some embodiments, resistance to rotational movements is provided by the width of the arms 404. In some embodiments, the arms 404 comprise a thickness of about 0.2 mm, optionally from about 0.1 mm to about 0.3 mm, optionally from about 0.05 mm to about 0.5 mm. In some embodiments, the arms 404 comprise a width of about 2.5 mm, optionally from about 2 mm to about 3 mm, optionally from about 1.5 mm to about 5 mm. In some embodiments, a relationship between the width of the arms and the thickness of the arms is of about 1/0.08, optionally of from about 1/0.01 to about 1/0.1, optionally from about 1/0.05 to about 0.5. In some embodiments, the arms 404 are made, for example, of stainless steel (for example, 302 stainless steel hard), and comprise an exemplary elastic modulus of about 200 GPa±20% and a yield strength of about 1110 MPa±20%.

Exemplary Implant Holder/Release Mechanism

Figure 6:
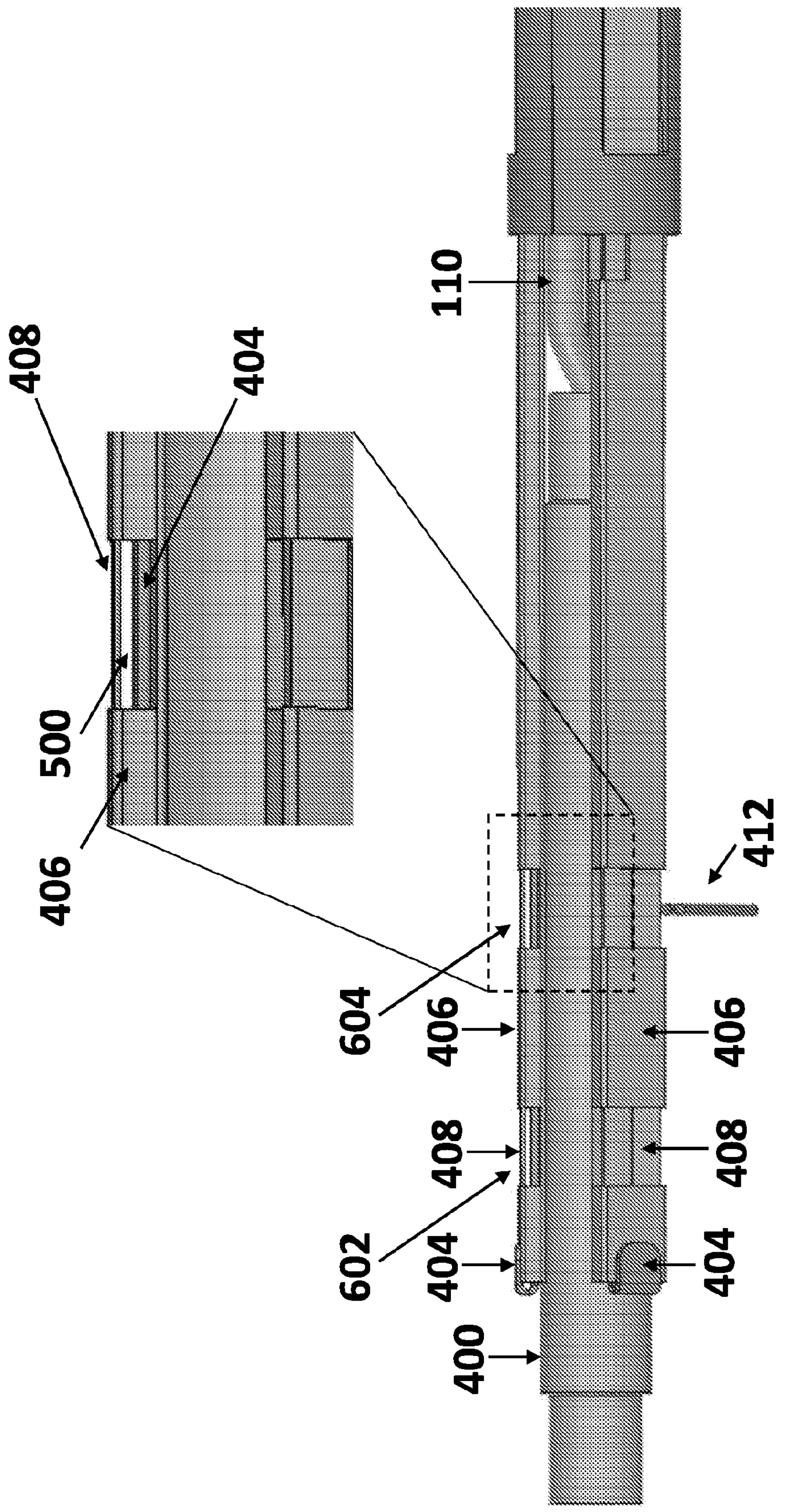
FIG. 6 is a schematic illustration of an exemplary implant holder/release mechanism located in the operational head, the operational head shown in a deflated configuration, according to some embodiments of the invention.

Referring now to FIG. 6, showing an exemplary implant holder/release mechanism located in the operational head, the operational head shown in a deflated configuration, according to some embodiments of the invention. In some embodiments, as disclosed above, the operational head comprises arms 404 that extend over the expandable body 400, as shown for example in FIG. 6. In FIG. 6, the expandable body 400 is in a deflated configuration (shown without the jacket 402). Also, as disclosed above, each arm 404 comprises the sleeve 406 and the movable implant holder 408. The zoom-in picture shows the space 500 created between the arm 404 and the movable implant holder 408. In some embodiments, space 500 is configured to house the implant 410 (not shown). In some embodiments, each arm comprises one or more locations comprising implant holding locations. In some embodiments, some implant holding locations are located close to the distal end of the device, thereby named distal implant holders 602, which are configured to hold a distal end and/or distal parts of the implant 410. In some embodiments, some implant holding locations are located close to the proximal end of the device, thereby named proximal implant holders 604, which are configured to hold a proximal end and/or proximal parts of the implant 410. In some embodiments, since the implant is wrapped around the operational head 106, as shown for example in FIG. 12*b*, the distal end of the implant 410 is held by one of the distal implant holders 602, then the implant is wrapped around the operational head so as to meet other implant holders until all implant holders comprise within them a part of the implant, and the proximal end of the implant is held by the last proximal implant holder 604.

Figure 7A:
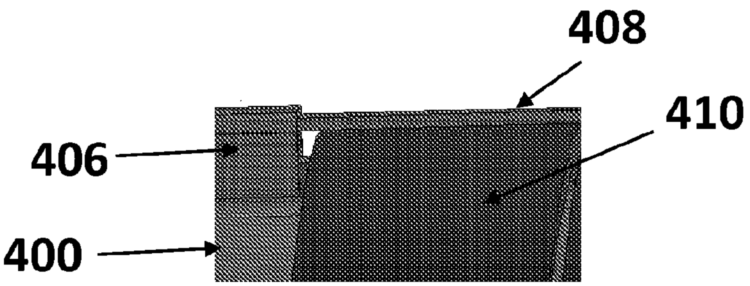
FIGS. 7*a*, 7*b*, 7*c*, 7*d*, and 7*e* are schematic illustrations of movement of a movable implant holder, according to some embodiments of the invention.
Figure 7B:
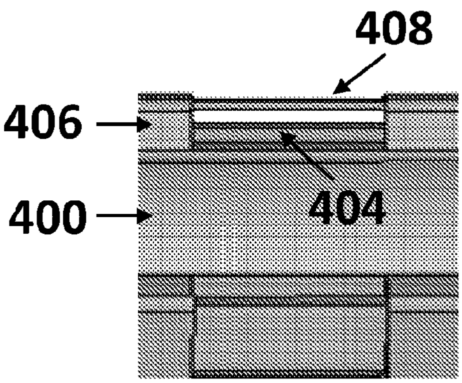
Figure 7C:
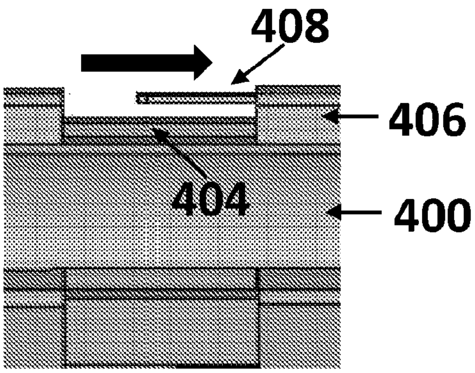
Figure 7D:
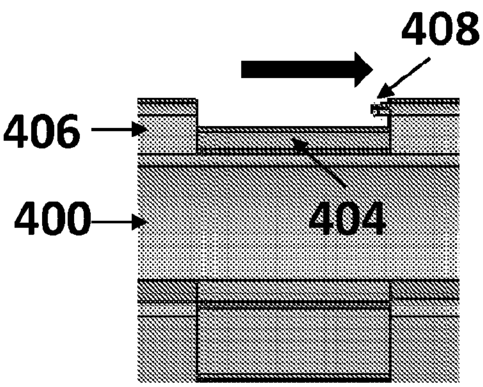
Figure 7E:
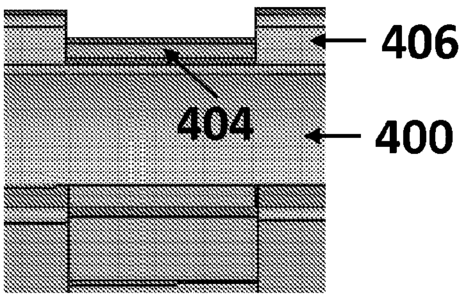

Referring now to FIGS. 7*a-e*, showing schematic illustrations of the movement of the movable implant holder 408, according to some embodiments of the invention. FIG. 7*a* shows an exemplary implant 410 disposed between the movable implant holder 408 and the arm 404 (not shown because it is hidden by the implant), while held together by the sleeve 406. FIGS. 7*b*-7*e* show an exemplary movement of the movable implant holder 408, according to some embodiments of the invention, without the implant (just for clarity purposes). As can be seen in FIG. 7*b*, the movable implant holder 408 is in its closed configuration, just before the beginning of the movement. FIG. 7*c* shows, following the arrow, the movement of the movable implant holder 408. FIG. 7*d* shows, following the arrow, the movement of the movable implant holder 408 almost at the end of the movement. FIG. 7*e* shows the movable implant holder 408 at its open configuration (movable implant holder 408 not actually shown since it is hidden by the sleeve 406), thereby allowing the release of the implant 410. In some embodiments, the proximal movement of the movable implant holder 408 causes firstly the release of the implant 410 from distal implant holders 602 and continuing the proximal movement will cause the release of the implant 410 from the proximal implant holders 604, thereby providing a controllable and controlled release of the implant.

Exemplary Tissue Cutter 412

Referring back to FIGS. 4*a* and 4*b*, in some embodiments, the operational head 106 comprises a tissue cutter 412 configured to cut the tissue of the urethra and create a space where the implant 410 will be implanted.

Figures 8A, 8B:
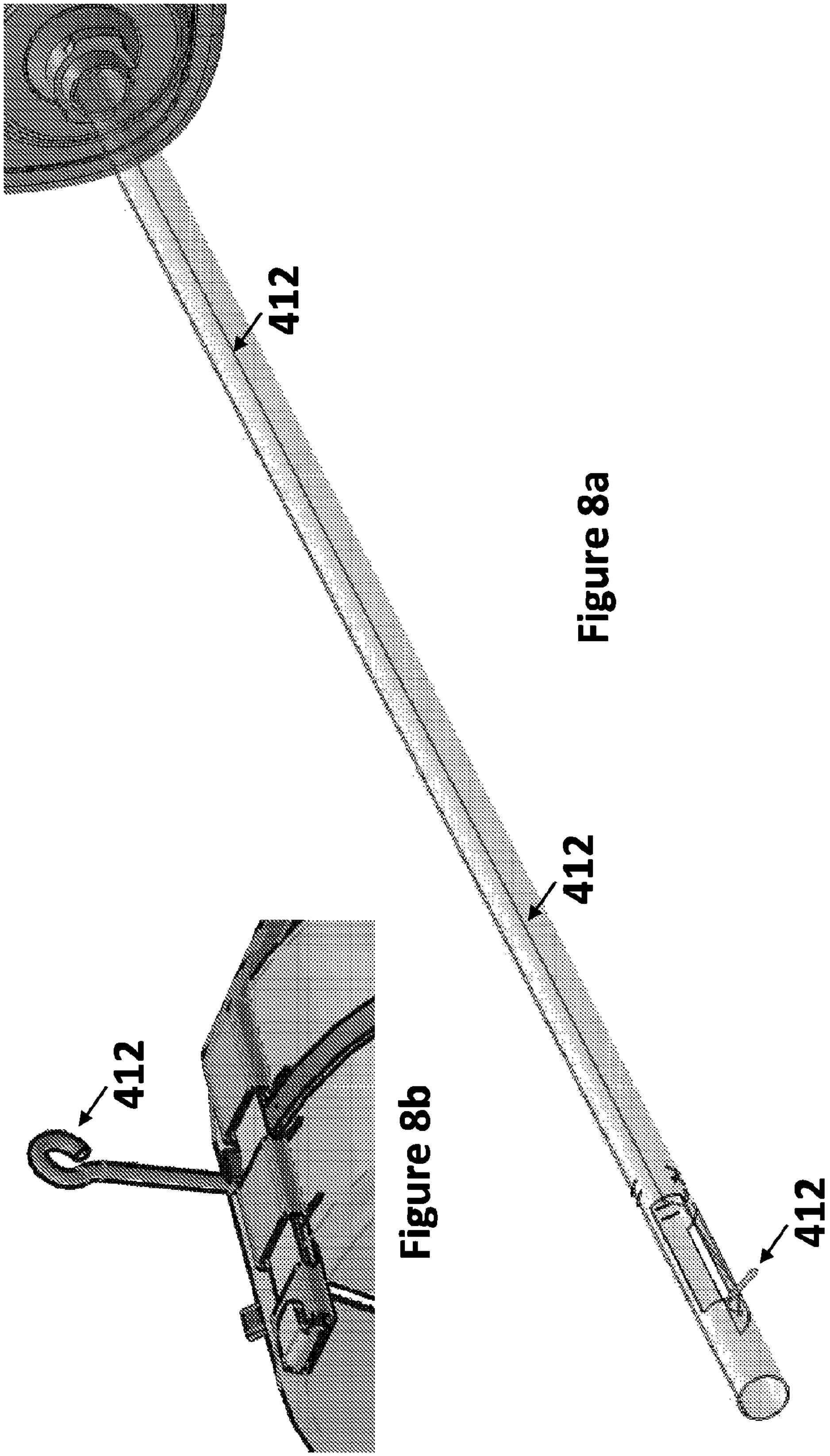
FIGS. 8*a* and 8*b* are schematic illustrations of exemplary tissue cutters positioned inside the shaft and outside the shaft, according to some embodiments of the invention.

Referring now to FIGS. 8*a-b*, showing a schematic representations of exemplary tissue cutters 412 inside the shaft 302 (FIG. 8*a*) and outside shaft 302 (FIG. 8*b*), according to some embodiments of the invention. In some embodiments, the tissue cutter 412 extends proximally at the handle and ends distally at the operational head of the device. In some embodiments, at the distal end, the tissue cutter 412 comprises a generally L-shaped operating configuration. In some embodiments, the tissue cutter 412 rotates (see below—methods) and the tissue cutter 412, with the distal end of the generally L-shaped operating configuration, while in contact with the surface of the tissue performs a cut while rotating. In some embodiments, the tissue cutter 412 is delivered to the treatment area in a retracted configuration. In some embodiments, the tissue cutter 412 is then released and assumes its L-shaped operating configuration when actuated by the user. In some embodiments, once the tissue cutter 412 has performed its function, the tissue cutter 412 is retracted proximally, to avoid causing unwanted damage to the tissue. In some embodiments, the tissue cutter 412 is configured to perform a cut in the tissue having a depth of from about 2 mm to about 10 mm. Optionally from about 1 mm to about 8 mm. Optionally from about 4 to about 15 mm. For example: 3 mm, 5 mm, 7 mm, 10 mm, 12 mm. In some embodiments, the tissue cutter 412 is made of a resilient metal, for example, nitinol, or stainless steel. In some embodiments, the tissue cutter is connected to an electrical or electromechanical energy, for example a diathermy machine or a piezoelectric transducer. In some embodiments, cutting the tissue comprises using an electrified tissue cutter.

In some embodiments, the head of the tissue cutter 412 comprises a rounded end, as shown for example in FIG. 8*b*, or a "T-like" shape (not shown), configured to provide a wider cut in a depth of the tissue while making a narrower cut on the surface of the tissue. In some embodiments, the length of the tissue cutter is from about 3 mm to about 10 mm. Optionally from about 5 mm to about 8 mm. Optionally from about 4 mm to about 6 mm. For example, 4 mm, 5 mm, 6 mm, 7 mm, 8 mm.

Figure 8C:
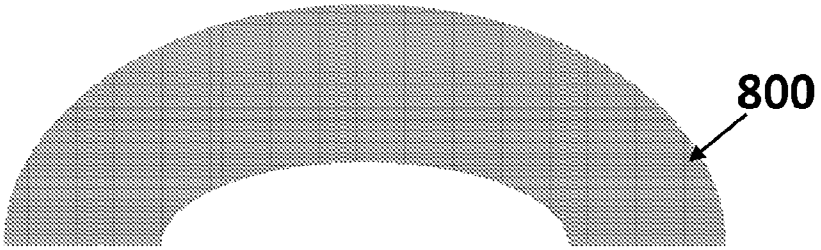
FIGS. 8*c*, 8*d*, 8*e*, 8*f*, and 8*g* are schematic illustrations of the cutting mechanism using a rounded head cutter, according to some embodiments of the invention.
Figure 8D:
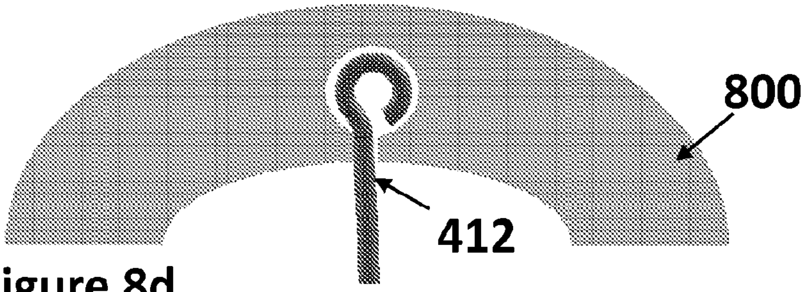
Figure 8E:
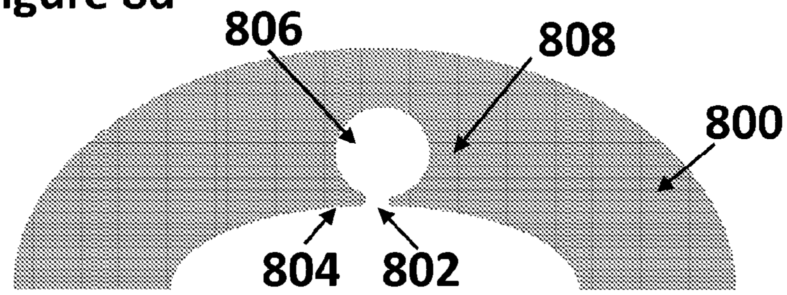
Figure 8F:
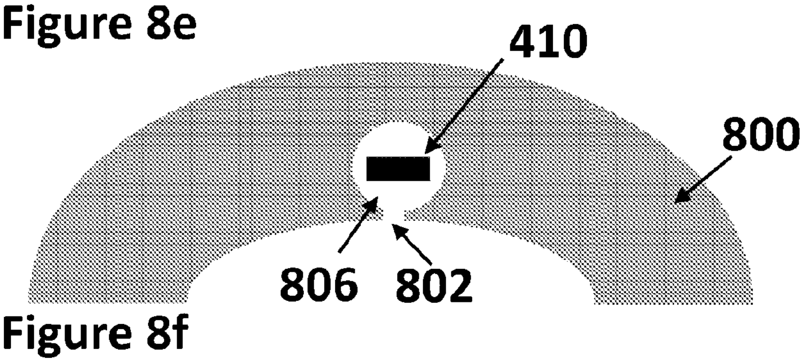
Figure 8G:
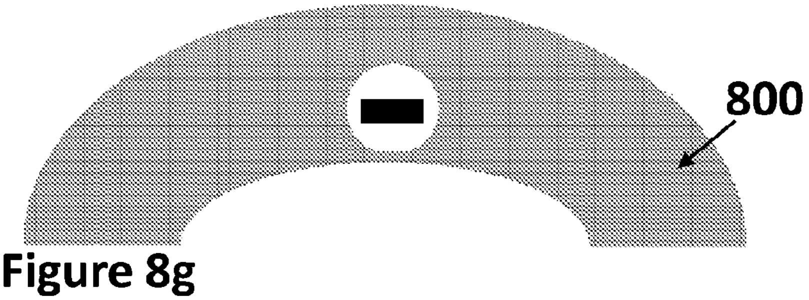

Referring now to FIGS. 8*c-g*, showing a schematic illustration of the cutting mechanism using a rounded head cutter, according to some embodiments of the invention. FIG. 8*c* shows a schematic illustration of the tissue 800, in which the cut is performed. In some embodiments, the rounded head cutter 412 performs a cut in the tissue, as shown for example in FIG. 8*d*. In some embodiments, due to the configuration of the cutter having a head comprises a rounded element, the cut that is done to define a narrow area 802 in the vicinity of the inner surface 804 (or optionally on the surface itself) of the tissue 800, while making a wider cut 806 in the internal part 808 of the tissue 800, as shown for example in FIG. 8*e*. In some embodiments, the implant 410 is then inserted through the narrow area 802 into the wider area of cut 806 in the tissue 800, as shown for example in FIG. 8*f*. In some embodiments, since the cut performed on the surface of the tissue is narrow, this potentially enables a quicker healing of the surface, thereby closing the implant 410 inside the tissue, as shown for example in FIG. 8*g*.

Figure 8H:
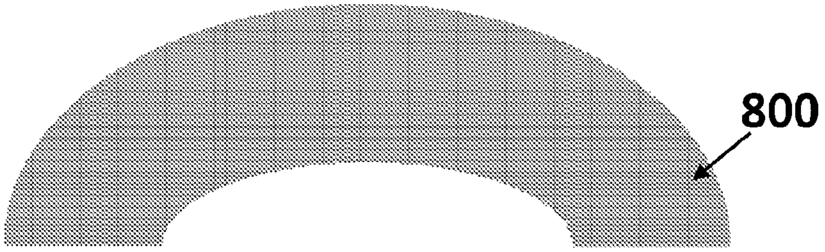
FIGS. 8*h*, 8*i*, 8*j*, 8*k*, and 8*l* are schematic illustrations of the cutting mechanism using a straight or "T-like" head cutter, according to some embodiments of the invention.
Figure 8I:
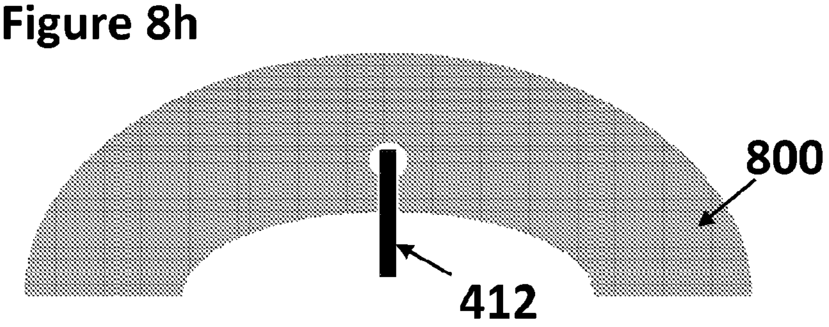
Figure 8J:
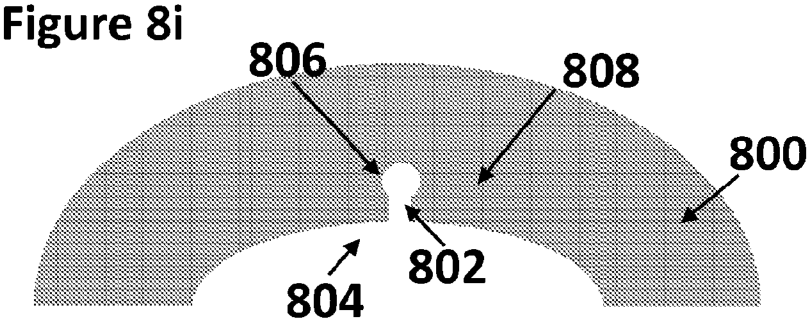
Figure 8K:
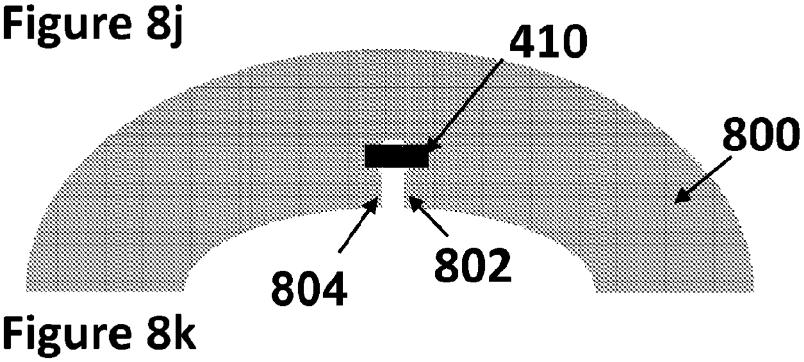
Figure 8L:
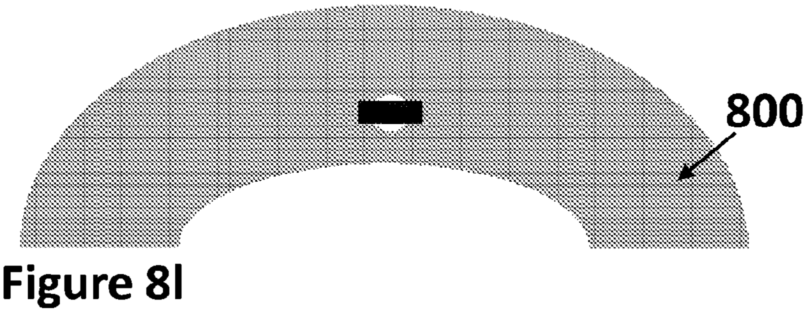

Referring now to FIGS. 8*h*-1, showing a schematic representation of the cutting mechanism using a straight or "T-like" head cutter, according to some embodiments of the invention. FIG. 8*h* shows a schematic representation of the tissue 800. In some embodiments, the head cutter 412 performs a cut in the tissue, as shown for example in FIG. 8*i*. In some embodiments, due to the configuration of the cutter having a straight head or a "T-like" head, the cut that is done comprises a narrow area 802 in the vicinity of the inner surface 804 (or optionally on the surface itself) of the tissue 800, while optionally making a wider cut 806 in the internal part 808 of the tissue 800, as shown for example in FIG. 8*j*. In some embodiments, the implant 410 is then inserted through the narrow area 802 into the optionally wider cut 806 in the tissue 800, as shown for example in FIG. 8*k*. In some embodiments, since the cut performed on the surface of the tissue is narrow, this potentially enables a quicker healing of the surface, thereby closing the implant 410 inside the tissue, as shown for example in FIG. 8*l*.

Figure 8M:
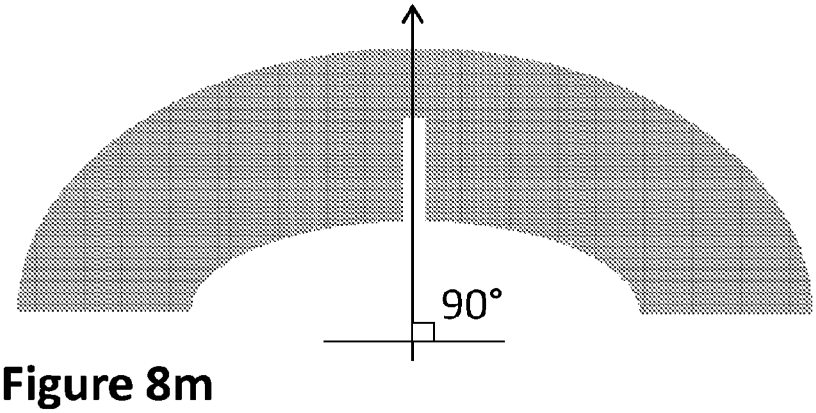
FIGS. 8*m* and 8*n* are schematic illustrations of the cutting angle, according to some embodiments of the invention.
Figure 8N:
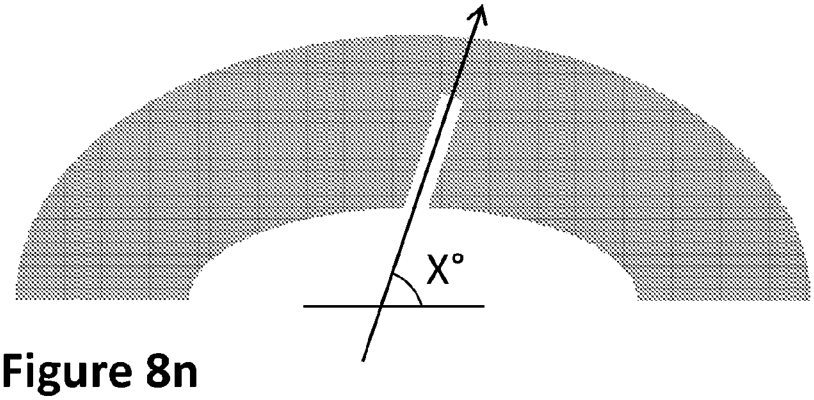

In some embodiments, the angle between the device and the cutter is 90 degrees, thereby when the cutter cuts the tissue, the cut is generally shaped to define a straight cut configuration, as schematically shown in FIG. 8*m*. In some embodiments, the angle between the device and the cutter is other than 90 degrees, thereby when the cutter cuts the tissue, the cut is shaped to define an angled configuration having an angle X, as schematically shown in FIG. 8*n*. In some embodiments, the angle is between about 45 degrees and about 89 degrees. Optionally between about 55 degrees and about 80 degrees. Optionally between about 60 degrees and about 75 degrees.

Figure 8O:
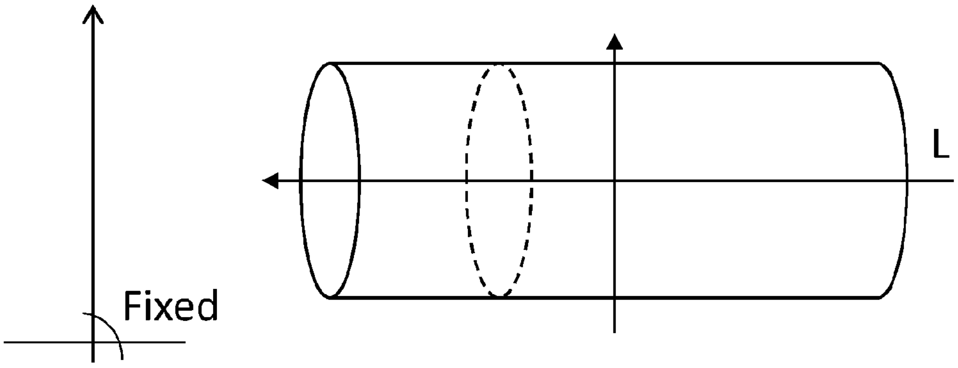
FIGS. 8*o* and 8*p* are schematic illustrations of a direction of an exemplary cut in tissue performed according to some embodiments of the invention.
Figure 8P:
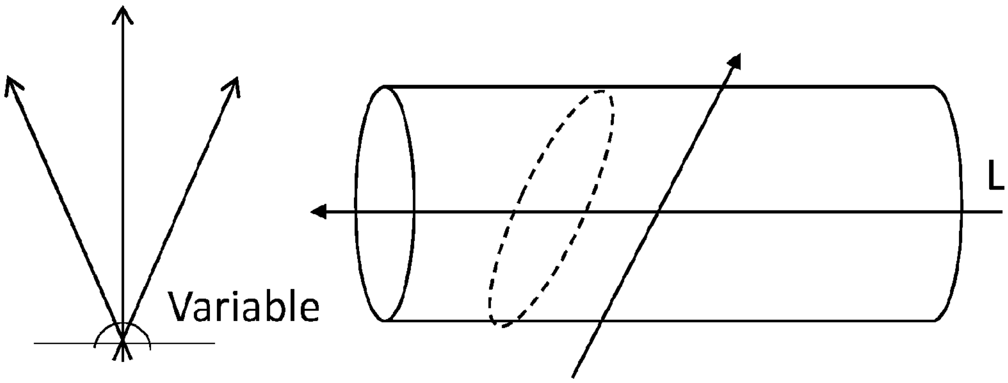

Referring now to FIGS. 8*o-p*, showing a schematic illustration of a direction of an exemplary cut, according to some embodiments of the invention. In some embodiments, the angle between the device and the cutter stays the same during the cutting action, thereby providing a cutting having a straight direction, as shown for example in FIG. 80. In some embodiments, the angle between the device and the cutter varies during the cutting action, thereby providing a cutting having a non-straight direction in relation to the longitudinal axis L of the urethra, as shown for example in FIG. 8*p*.

Exemplary Internal Guiding Element 114

Figure 9A:
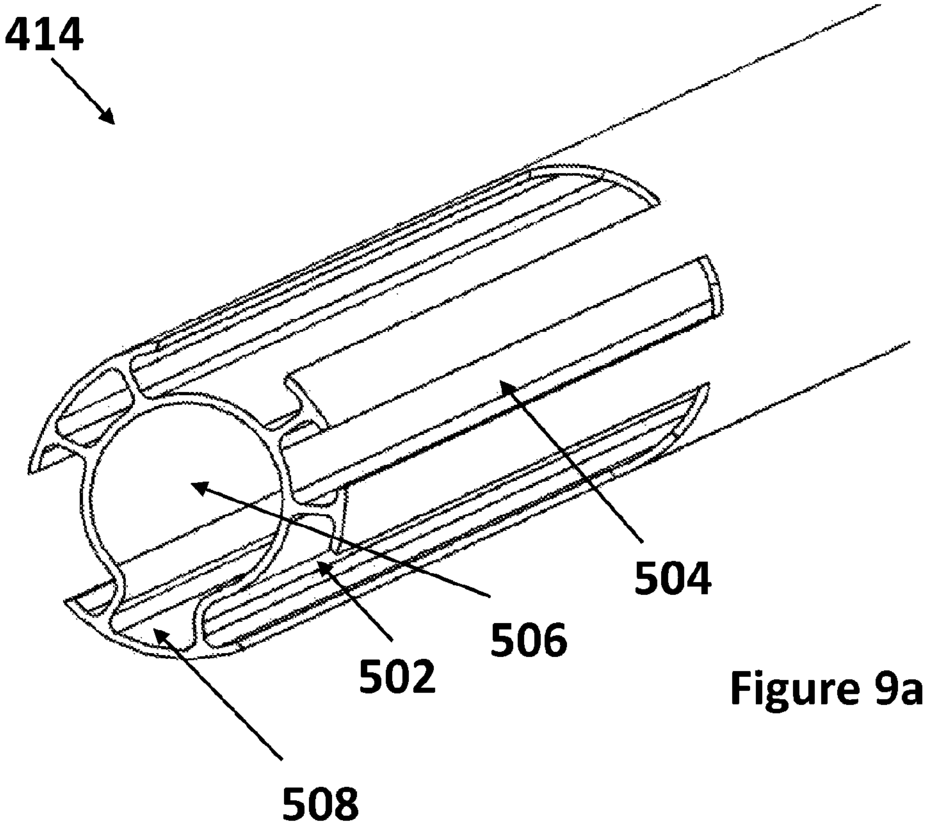
FIGS. 9*a*, 9*b*, and 9*c* are schematic illustrations of different views of an exemplary internal guiding element, according to some embodiments of the invention.
Figure 9B:
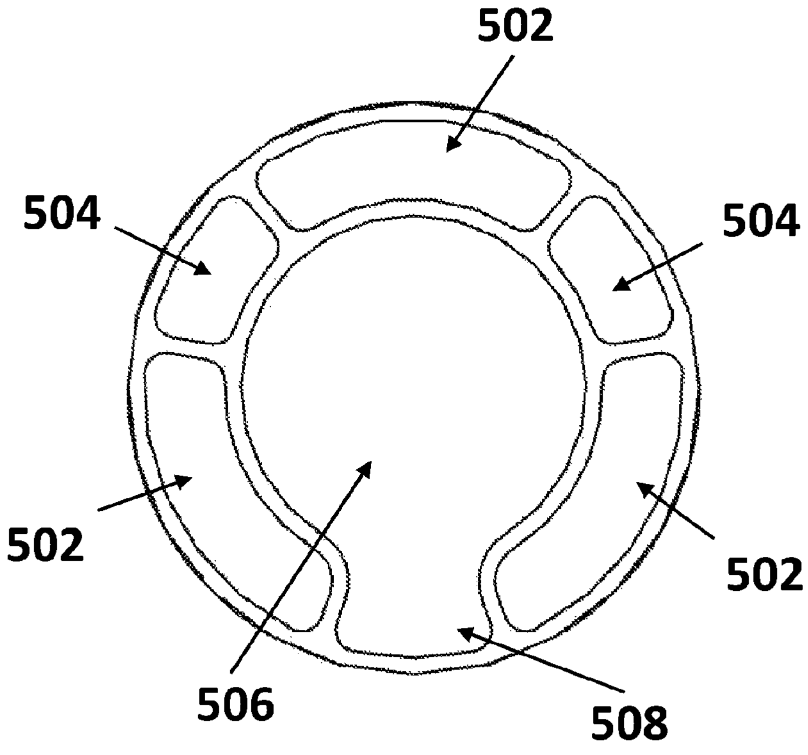
Figure 9C:
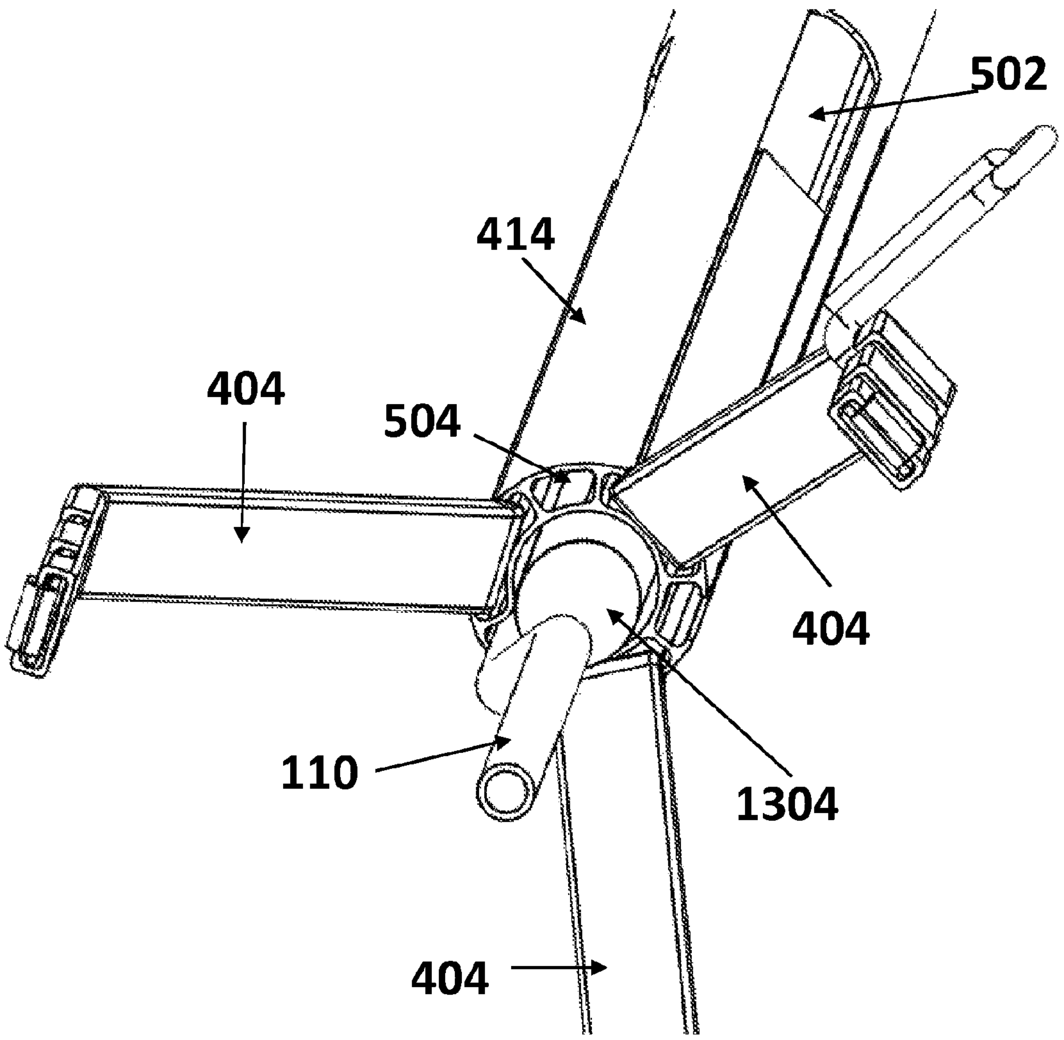

Referring now to FIGS. 9*a-c*, showing different view of an exemplary internal guiding element, according to some embodiments of the invention. In some embodiments, inside the shaft 302 there can optionally be an internal guiding element 414 configured to separate between the different parts that run from the handle 100 to the distal end of the device. In some embodiments, the internal guiding element comprises one or more channels 502, 504, 506, 508 configured to house different parts, while optionally keeping them separated from each other, as shown for example in FIGS. 9*a-b*. In some embodiments, the internal guiding element 414 comprises an internal hollow channel 506. In some embodiments, internal guiding element 414 comprises channels having different width, different depth, same width, same depth, and any combination thereof. In the exemplary internal guiding element 414 shown in FIGS. 9*a-c*, channels 502 are configured to house, in some embodiments, the arms 404, optionally the arms 404 with the sleeve 406, optionally the arms 404 with the movable implant holder 408, optionally the arms 404 with the movable implant holder 408 with the sleeve 406. In some embodiments, channels 502 also comprise the function to enable and assist with the rotational movement of the components located at the distal end, the rotational movement arriving from the handle to the distal end of the device. In some embodiments, channel 508 is configured to house the tube 110 connecting between the expandable body 400 and the inlet/outlet 108. In some embodiments, channel 504 is configured to one or more of housing and isolating the tissue cutter 412. In some embodiments, channel 506 is configured to house additional components used during the procedure, for example an optical element (e.g. micro camera—see below). FIG. 9*c* shows a schematic image of the internal guiding element 414 with some of the different parts of the system.

Exemplary Handle and Mechanisms Therein

Figure 10:
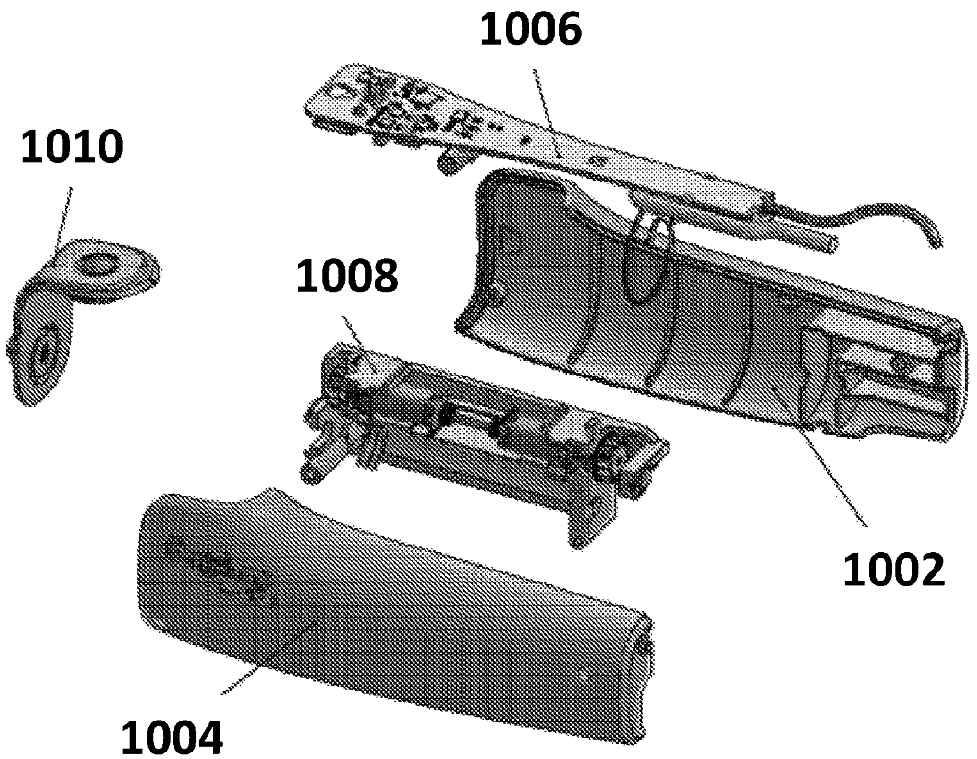
FIG. 10 is a schematic illustration of an exploded view of an exemplary handle according to some embodiments of the invention.

Referring now to FIG. 10, showing an exploded view of a schematic illustration of an exemplary handle according to some embodiments of the invention. In some embodiments, the handle 100 comprises dedicated covers 1002/1004 for the internal mechanisms in the handle 100, the electronic hardware 1006, the internal actuation elements 1008 and a frontal cover 1010 comprising the aperture for the shaft and the user control button(s). In some embodiments, the electronic hardware 1006 comprises a controller configured to synchronize between the actions performed by the device. In some embodiments, the actions of the device that are potentially synchronized includes one or more of activating motors to perform linear and/or rotational movements, inflating/deflating expandable body, exposing and/or retracting the cutter, exposing and/or retracting the operational distal end. In some embodiments, the controller is a mechanical controller. In some embodiments, the controller is an electronic controller.

Exemplary Internal Actuation Elements

Figure 11A:
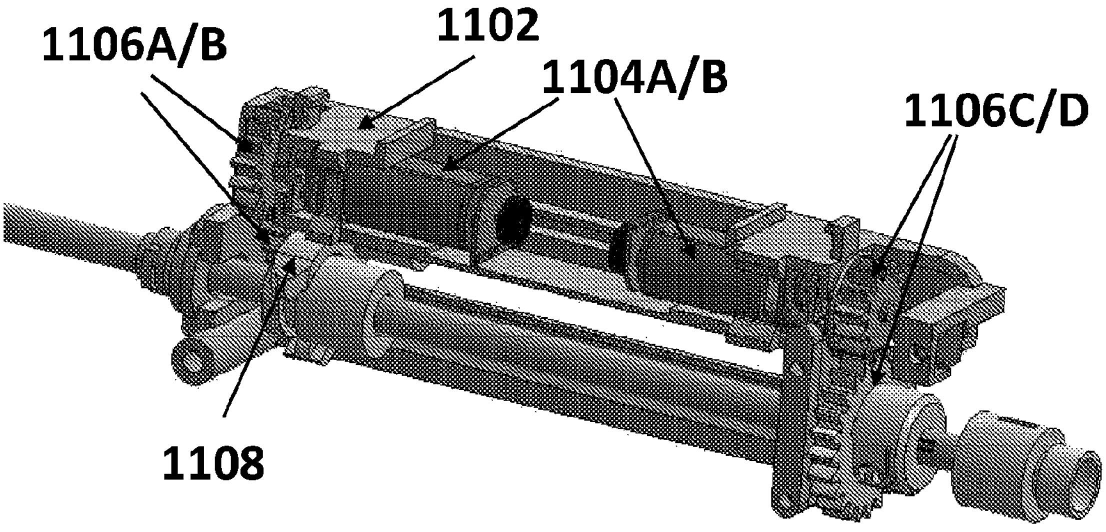
FIGS. 11*a* and 11*b* are a schematic isometric view (FIG. 11*a*) and an exploded view (FIG. 11*b*) of an exemplary internal actuation mechanism, according to some embodiments of the invention.
Figure 11B:
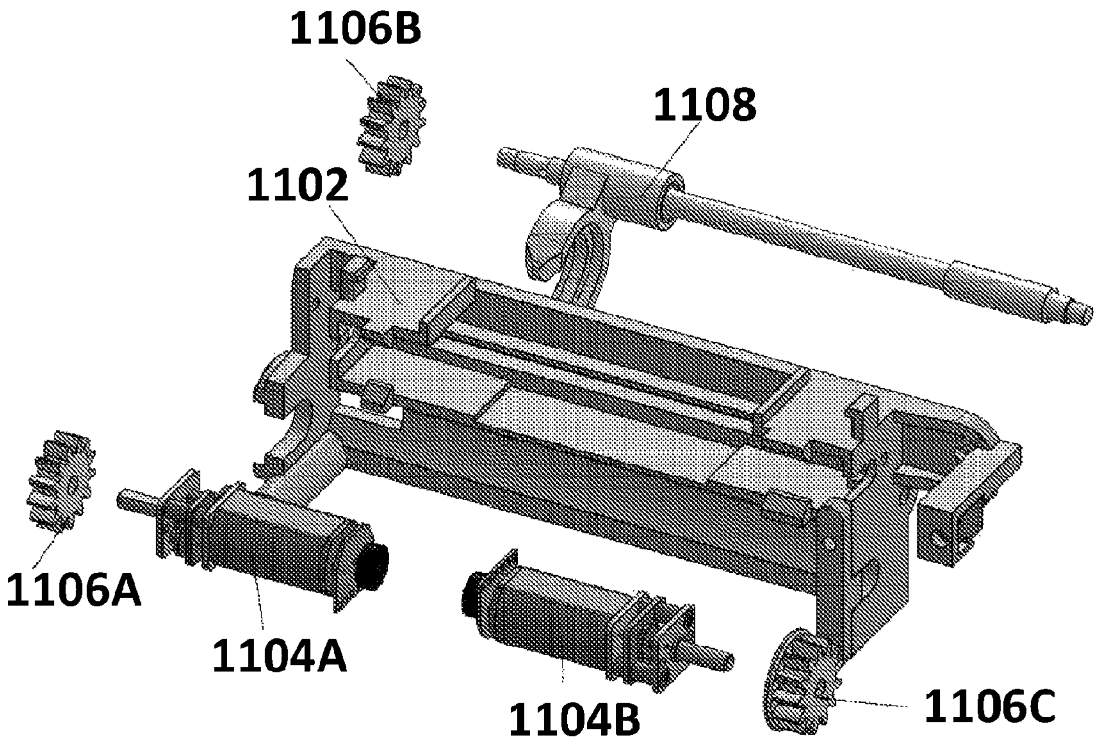

Referring now to FIGS. 11*a-b*, showing a schematic isometric view (a) and exploded view (b) of an exemplary internal actuation mechanism, according to some embodiments of the invention. In some embodiments, the internal actuation mechanisms are held by a chassis 1102 and one or more auxiliary/actuating rods/sleeves 1108. In some embodiments, the internal actuation mechanisms comprise one or more motors 1104 configured to actuate mechanisms at the distal end of the device using of one or more gears 1106/306. In some embodiments, the one or more motors 1104 are configured to rotate and/or actuate and/or move one or more of the elongated body 104, the shaft 302, the internal operational element 300, the operational head 106, the movable implant holders 408, the tissue cutter 412, and any combination thereof. In FIG. 11*a*, the exemplary internal actuation mechanism is shown with the shaft 302, as an example. In some embodiments, the one or more motors 1104 are the same. In some embodiments, the one or more motors 1104 are different. In some embodiments, the one or more motors 1104 are configured to operate at a velocity of from about 1 RPM to about 1000 RPM, optionally from about 1 RPM to about 500 RPM, optionally from about 1 RPM to about 75 RPM.

In some embodiments, the distal motor 1104A rotates gear 1106A which then rotates gear 1106B which actuate the proximal/distal movement of the elongated body 104 (held by connector 204) on the rod 1108. In some embodiments, the motor provides a force of from about 1 Kg to about 5 Kg. Optionally from about 2 Kg to about 8 Kg. Optionally from about 3 Kg to about 10 Kg. For example, 1 Kg, 2 Kg, 3 Kg, 4 Kg. In some embodiments, the motor provides a proximal-distal (or vice versa) movement at a velocity of from about 1 mm/s to about 10 mm/s. Optionally from about 2 mm/s to about 20 mm/s. Optionally from about 4 mm/s to about 30 mm/s. For example, 2 mm/s, 4 mm/s, 8 mm/s, 15 mm/s.

In some embodiments, the proximal motor 1104B rotates gears 1106C and 1106D (also numbered gear 306 in FIG. 3) which actuate rotational movement of the shaft 302. In some embodiments, the motor 1104B is configured to provide shaft 302 with a rotational force (torque) of from about 50 Nmm to about 300 Nmm. Optionally from about 80 Nmm to about 500 Mnn. For example, 90 Nmm, 100 Nmm, 112 Nmm, 120 Nmm. In some embodiments, the velocity of rotation of the shaft 302 is of from about 1 rotation per second to about 1 rotation per 3 seconds. Optionally from about 1 rotation per 0.5 second to about 1 rotation per 5 seconds. For example, 1 rotation in 1 second, 1 rotation in two seconds, 1 rotation in 3 seconds.

Exemplary Implants

Figure 12A:
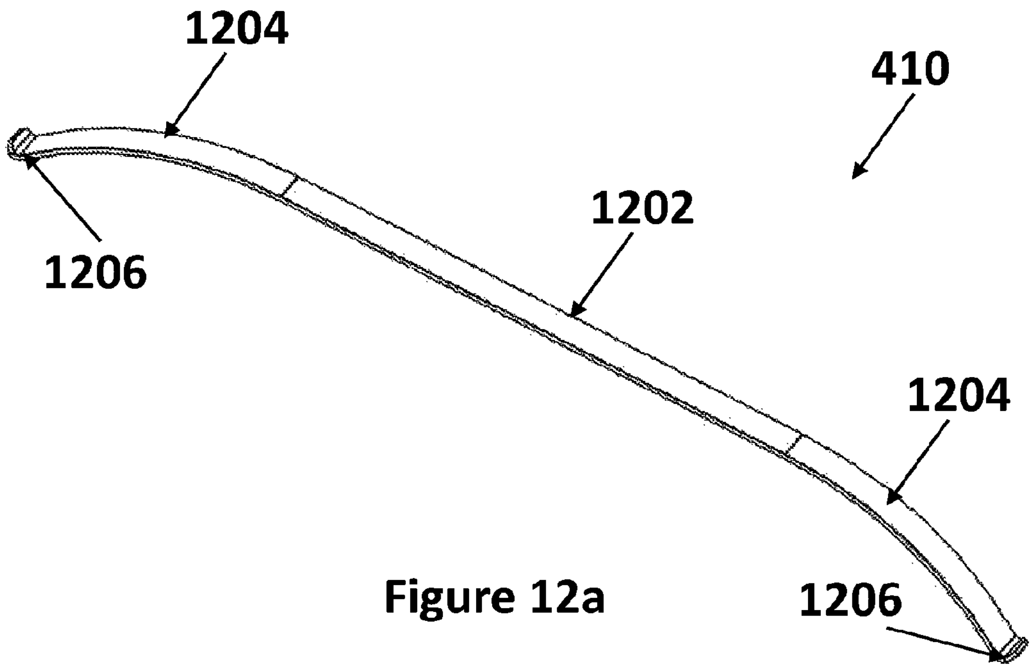
FIGS. 12*a*, 12*b*, 12*c*, and 12*d* are schematic illustrations of exemplary implants, according to some embodiments of the invention.
Figure 12B:
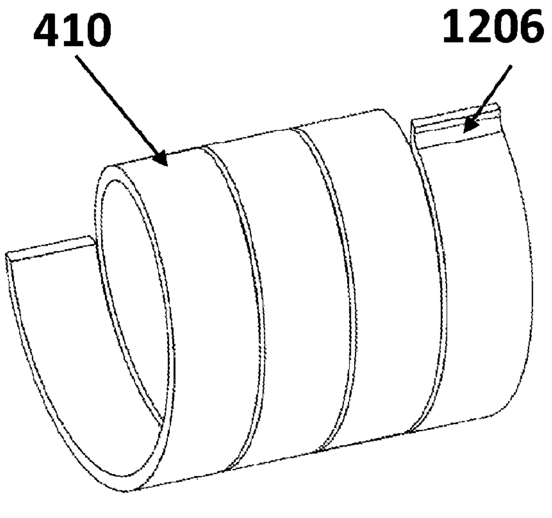

Referring now to FIGS. 12*a-d*, showing exemplary implants 410, according to some embodiments of the invention. FIG. 12*a* shows an exemplary implant 410 in an open configuration, while FIG. 12*b* shows an exemplary implant in a folded spiral configuration. In some embodiments, the implant 410 is made of a suitable resilient material, for example one or more of stainless steel, nitinol, titanium, PET, PEEK, PA. In some embodiments, the implant 410 comprises a length of from about 50 mm to about 70 mm. Optionally from about 40 mm to about 80 mm. Optionally from about 30 mm to about 100 mm. For example, 50 mm, 60 mm, 70 mm, 80 mm. In some embodiments, the implant 410 comprises a thickness of from about 0.01 mm to about 1 mm, optionally from about 0.1 mm to about 0.8 mm, optionally from about 0.3 to about 0.6 mm, for example 0.1 mm, 0.25 mm, 0.3 mm, 0.5 mm. In some embodiments, the implant 410 comprises a width of from about 0.5 mm to about 4 mm, optionally from about 0.7 mm to about 2 mm, optionally from about 1 mm to about 1.5 mm, for example. 0.5 mm, 0.7 mm, 1 mm, 1.3 mm, 2 mm, 3 mm. In some embodiments, a potential advantage of making implants having a short width is that implants having a short width allow the tissue around the implant to close and heal better, and they allow the implants to be inserted deeper in the cut.

In some embodiments, the implant 410 is manufactured straight. In some embodiments, the implant 410 is manufactured slightly curved. In some embodiments, the implant 410 comprises a middle straight section 1202 and two slightly curved end sections 1204 (e.g., end sections 1204 are also referred to herein as the proximal and distal portions of the implant), as shown for example in FIG. 12*a*. It is noted that for some embodiments, end sections 1204 are shaped to define straight end sections/portions when implant 410 is unconstrained. In some embodiments, at the end sections of the implant 410, the implant is folded thereby creating protrusions 1206, as shown for example in FIGS. 12*a-b*. In some embodiments, the folded portion (protrusion) is used to hold the implant between the arm and the movable implant holder 408. In some embodiments, the foldings (protrusions) 1206 at the end of the implant provide further anchoring elements once inside the cut. In some embodiments, the shape of the implant is configured to provide the implant with an increased range of the forces that the implant applies on the tissue wall. In some embodiments, the forces applied by the implant to the walls of the urethra are of from about 50 gr to about 100 gr. Optionally from about 40 gr to about 150 gr. Optionally from about 25 gr to about 500 gr. For example 50 gr, 60 gr, 70 gr, 100 gr, 120 gr.

Figure 12D:
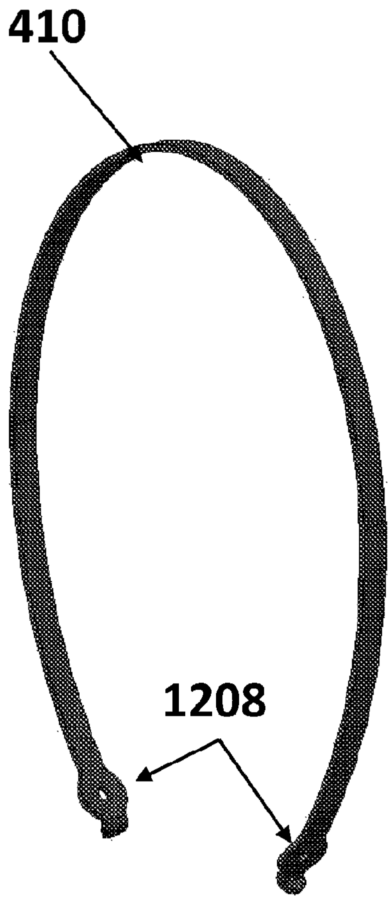
Figure 12C:
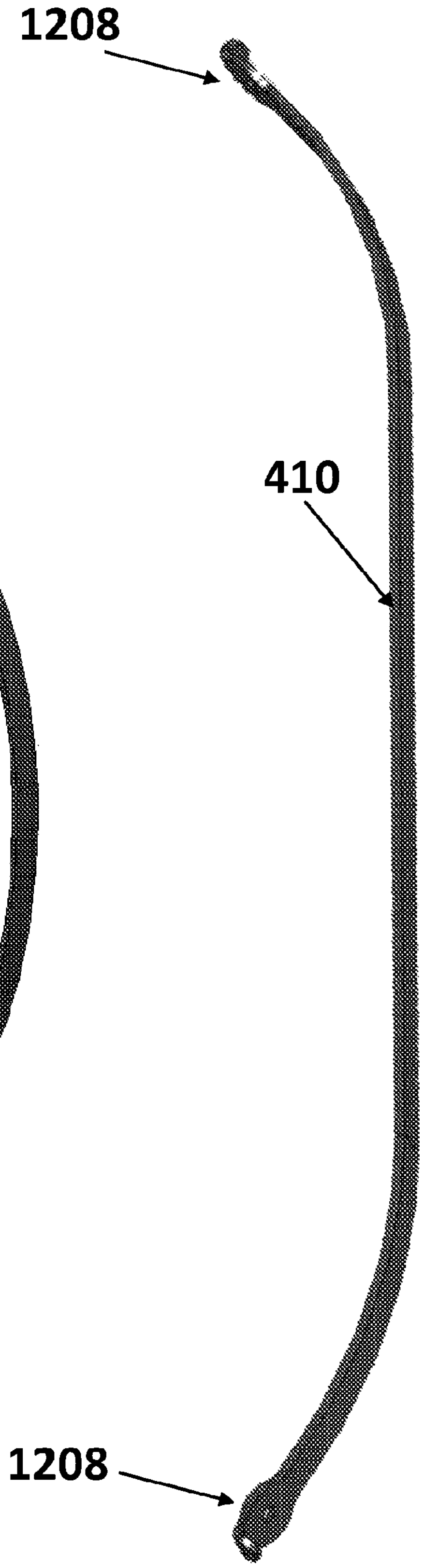

Typically, implant 410 is made of a shape-memory alloy, such as nitinol. Typically, the shape-memory alloy of the implant is shape set such that the implant assumes a generally straight shape at least along middle section 1202 when in an unconstrained state (i.e., in the absence of any forces being applied to implant 410). Since the implant 410 is made of shape-memory materials that tend to return to their natural open state, once released from the delivery device, the implant will try to return to its shape set, open state, which is substantially straight, thereby pushing the walls of the urethra with an increase force, when compared to an implant that is not substantially straight. In some embodiments, the inflation of the expandable body helps the implant to return to the desired configuration. FIGS. 12*a* and 12*c* show exemplary implants in their natural open state having a generally straight configuration. FIG. 12*d* shows the form that the implant will take inside the cut on the wall of the urethra once implanted. As shown in FIG. 12*d*, implant 410 is implanted in the tissue in a curved configuration. In some embodiments, due to the resistance created by the walls of the urethra, the implant is not be able to return to its straight configuration, thereby continuing pushing the walls and thereby opening the obstruction of the urethra.

Typically, the shape-memory material of the implant is shape set such that the implant assumes a generally straight shape along more than 50 percent (e.g., more than 60 percent or more than 70 percent) of its length when in an unconstrained state (i.e., in the absence of any forces being applied to the implant). (In some instances, such an implant is described herein as a "quasi-straight implant".) Typically, upon implantation of the implant in the cut formed in the urethra, the implant is constrained into a curved shape by the tissue in which the implant is implanted. Due to the tendency of the shape-memory alloy to return to its pre-set generally straight configuration, the implant applies radially outward pressure to the tissue. By being shape set in the above-described manner, the implant typically dilates the urethra more effectively than if the implant were to be shape set such as to define a less generally straight shape.

In some embodiments, the implant comprises pad-like endings 1208, as shown for example in FIGS. 12*c-d*. In some embodiments, the pad-like endings 1208 contribute to one or more of: the correct placement of the implant inside the cut by not allowing the implant to rotate on its axis once inside the cut and/or potentially avoiding perforating and/or damaging the tissue once inside the cut.

In some embodiments, the implant comprises one or more protrusions configured to stabilize the implant once implanted in the implantation site inside the cut, the protrusions configured to be blunt so they will not damage the tissue.

In some embodiments, the implant is removed after a predetermined period of time, for example 3 months, 6 months, 12 months or 36 months. Alternatively, the implants are formed of a material that is biodegradable. In some embodiments, the implants biodegrade over a period of time chosen by the doctor, for example 3 months, 6 months, 12 months or 36 months.

Exemplary Additional Hardware

Figure 13A:
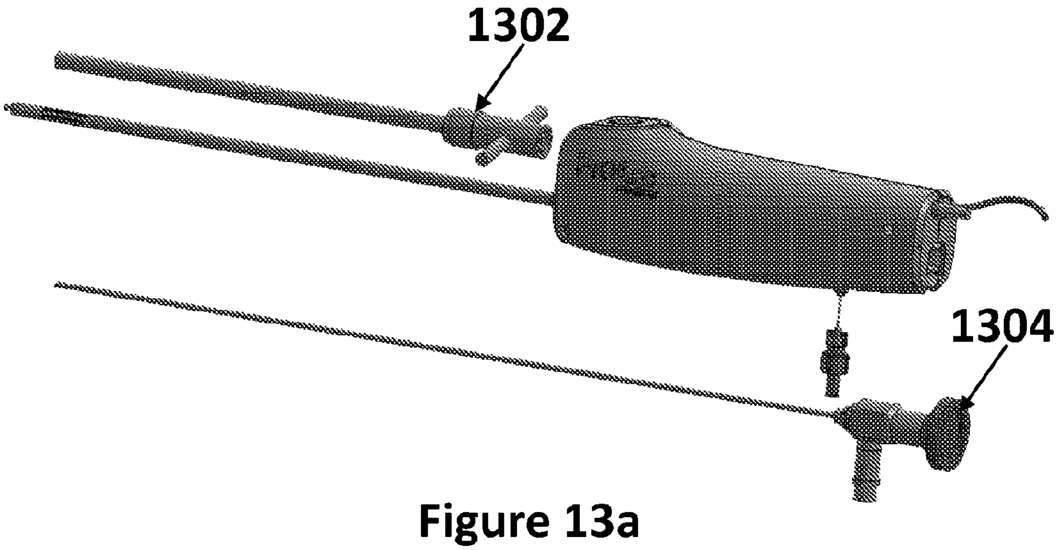
FIGS. 13*a* and 13*b* are schematic illustrations of additional exemplary hardware used with the device for dilating a urethra of a subject at least partially obstructed by an enlarged prostate, according to some embodiments of the invention.
Figure 13B:
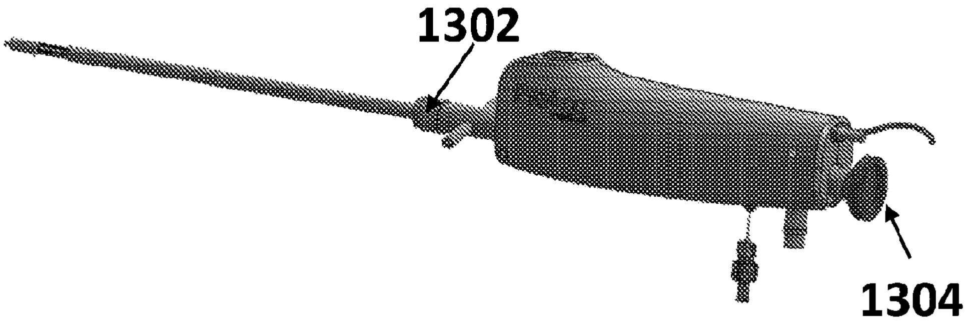

Referring now to FIGS. 13*a-b* and 14*a-b*, showing two exemplary additional hardware used with the device for dilating a urethra of a subject at least partially obstructed by an enlarged prostate, according to some embodiments of the invention. In some embodiments, the device is used together with an outer sheath 1302. In some embodiments, the device further comprises an optical element 1304. FIG. 13*a* shows the device separated from the additional hardware of outer sheath 1302 and optical element 1304, while FIG. 13*b* shows the device with the additional hardware outer sheath 1302 and optical element 1304 incorporated therein.

Exemplary Outer Sheath (Obturator)

In some embodiments, an outer sheath (obturator) 1302 is used during the treatment, as known in the art. In some embodiments, the outer sheath (obturator) 1302 is sized and shaped to house the device.

Exemplary Optical Element (Camera)

Figure 14A:
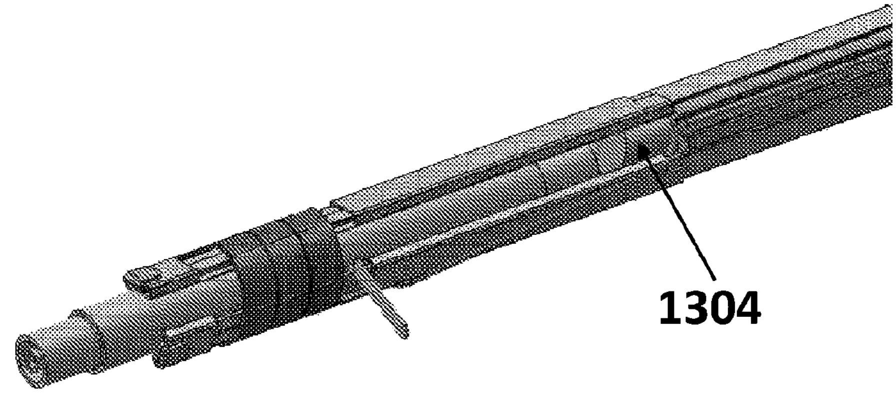
FIGS. 14*a* and 14*b* are schematic illustrations of additional exemplary hardware used with the device for dilating a urethra of a subject at least partially obstructed by an enlarged prostate, according to some embodiments of the invention.
Figure 14B:
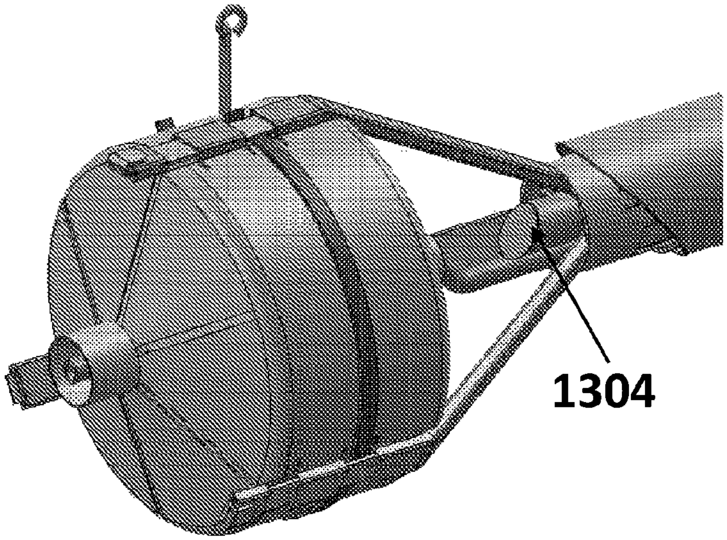

Referring now to FIGS. 14*a-b*, showing the distal end of an exemplary optical element, for example a camera, at the distal end of the device, according to some embodiments of the invention. In some embodiments, the device further comprises the optical element 1304, which extends from the proximal end of the device until slightly beyond the end of the shaft, about ±2 mm of the end of the shaft. In some embodiments, the optical element extends until before the expandable body. In some embodiments, the optical element comprises a field of view of from about 0 degrees (meaning looking forward) to about ±90 degrees, optionally from about 0 degrees to about ±70 degrees, optionally from about 0 degrees to about ±120 degrees. In some embodiments, the optical element is configured to allow the user to navigate through the urethra, visualize the location of the prostate, and place the implant under direct visualization at and of the desired place.

Exemplary Methods

Exemplary Manual Method

Figure 15:
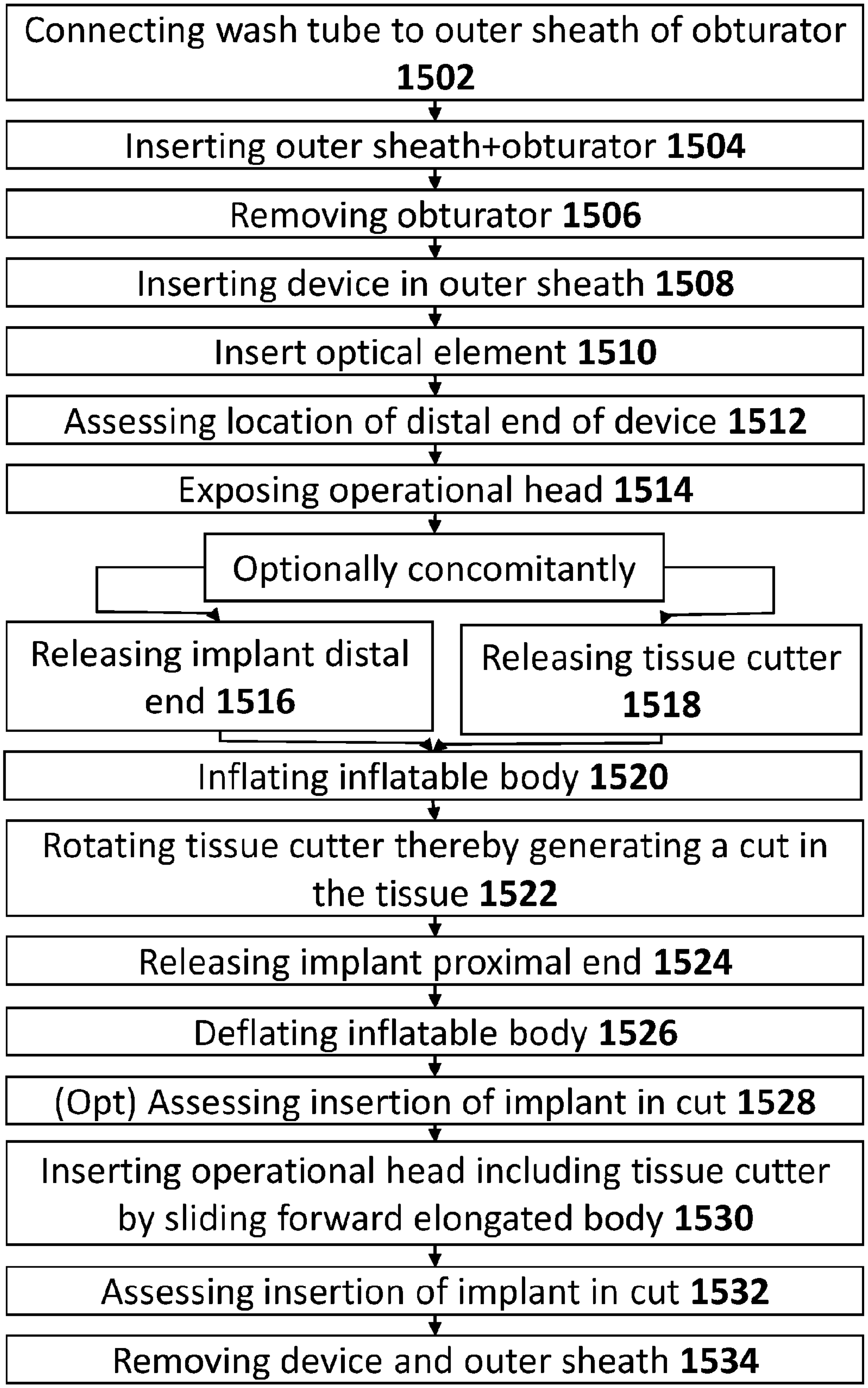
FIG. 15 is a flowchart showing an exemplary method practiced according to some embodiments of the invention.

Referring now to FIG. 15 showing a flowchart disclosing an exemplary method practiced, according to some embodiments of the invention. In some embodiments, the following method is followed by a user during the operation of the device. In some embodiments, the method begins by connecting a wash tube to the outer sheath of an obturator 1502. Then, the user inserts the outer sheath with the obturator in the patient 1504. Then the user removes the obturator, leaving the outer sheath in place 1506. Then the user inserts the device in the outer sheath 1508. In some embodiments, optionally, the user then inserts the optical element (e.g., a camera) inside the device 1510. In some embodiments, the user then assesses the location of the distal end of the device by means of the optical element (camera) 1512. In some embodiments, the operational head is then exposed beyond the distal end of the device 1514 by retracting (moving proximally) the elongated body 104 from about 30 mm to about 40 mm, preferably 36 mm. In some embodiments, then the distal end of the implant is released from device 1514 by further retracting (moving proximally) the elongated body 104 from about 3 mm to about 7 mm, preferably 5 mm. In some embodiments, releasing the distal end of the implant allows the expandable body to be inflated, since if both ends of the implant are trapped, the implant will hold the arms therefore not permitting the arms to extend providing the expandable body with the necessary space to be inflated. In some embodiments, then the tissue cutter 1518 is then released. In some embodiments, up to this point, the tissue cutter is held inside the outer tube of the device. In some embodiments, only when cutting is required, the tissue cutter is released from the outer tube. In some embodiments, optionally, the releasing of the implant distal end 1516 and the releasing of the tissue cutter 1518 are performed concomitantly. In some embodiments, then the expandable body is inflated 1520. In some embodiments, the inflation of the expandable body extends the recently one side released implant, from its folded confirmation to its expanded configuration. In some embodiments, then the tissue cutter is rotated thereby generating a cut in the tissue 1522. In some embodiments, rotation of the cutter is performed by rotating the outer tube together with all the components inside of it. In some embodiments, the following action is the release of the proximal end of the implant 1524 by further retracting (moving proximally) the elongated body 104 from about 5 mm to about 9 mm, preferably 7 mm.

In some embodiments, the release of the proximal end of the implant will allow the implant to unwind from the folded helical configuration (the folded configuration shown in FIG. 12*b*) into a curved configuration in which it is released and implanted into the cut (the curved configuration as shown in FIG. 12*d*). Since the release of the implant is performed in vicinity to the cut, the implant enters the cut. In some embodiments, then the expandable body is deflated 1526. In some embodiments, optionally at this point the user can assess the insertion of the implant in the cut 1528. In some embodiments, then the operational head is inserted back into the elongated body for subsequent removal from the body by sliding forward the elongated body, optionally together with the tissue cutter 1530. In some embodiments, optionally the user then assesses (again if done before or for the first time if not performed before) the deployment of the implant in the cut 1532. In some embodiments, the method ends by removing the device with the outer sheath from the body of the patient 1534.

Exemplary Semi-Automatic Method

Figure 16:
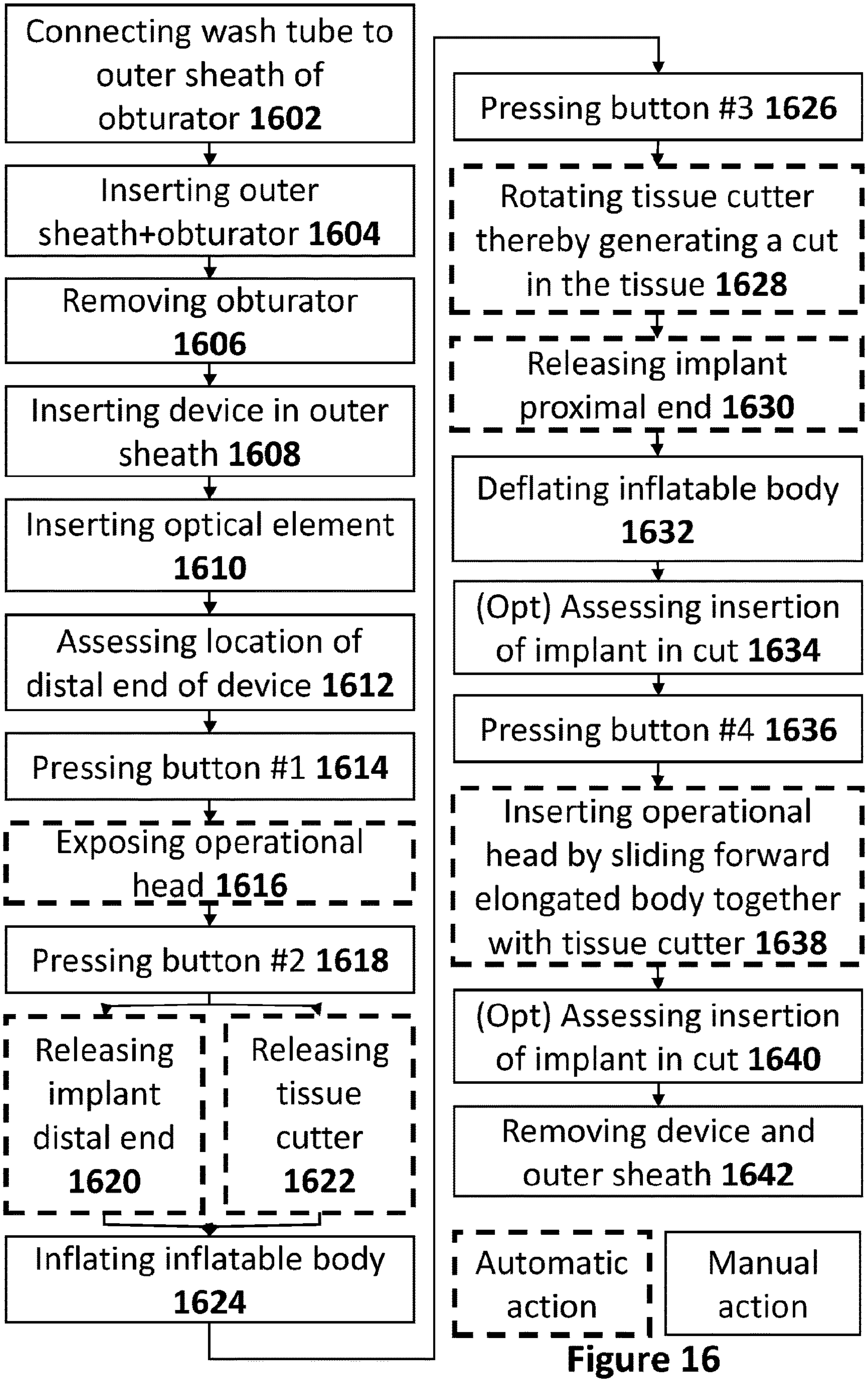
FIG. 16 is a flowchart showing an exemplary semi-automatic method practiced according to some embodiments of the invention.

Referring now to FIG. 16 showing a flowchart disclosing an exemplary semi-automatic method practiced, according to some embodiments of the invention. In some embodiments, the following semi-automatic method is followed by a user during the operation of the device. In the flowchart solid squares are manual actions, while dashed squares are automatic actions activated by the user (for example, by pushing a button). In some embodiments, the method begins by connecting a wash tube to the outer sheath of an obturator 1602. Then, the user inserts the outer sheath with the obturator in the patient 1604. Then the user removes the obturator, leaving the outer sheath in place 1606. Then the user inserts the device in the outer sheath 1608. In some embodiments, optionally, the user then inserts the optical element (e.g., a camera) inside the device 1610. In some embodiments, the user then assesses the location of the distal end of the device by means of the optical element (camera) 1612. In some embodiments, the user presses the button for the first time 1614, which causes the operational head to automatically be exposed beyond the distal end of the device 1616 by retracting (moving proximally) the elongated body 104 from about 30 mm to about 40 mm, preferably 36 mm. In some embodiments, the user then presses the button for the second time 1618, which causes the automatic release of the distal end of the implant 1620 by further retracting (moving proximally) the elongated body 104 from about 3 mm to about 7 mm, preferably 5 mm. In some embodiments, releasing the distal end of the implant allows the expandable body to be inflated, since if both ends of the implant are trapped, the implant will hold the arms therefore not permitting the arms to extend providing the expandable body with the necessary space to be inflated. In some embodiments, optionally, concomitantly with the release of the distal end of the implant 1620, the tissue cutter is automatically released 1622. In some embodiments, then the inflatable body is manually inflated 1624. In some embodiments, the inflation of the expandable body extends the recently one side released implant, from its folded confirmation to its expanded configuration. In some embodiments, the user then presses the button for the third time 1626, which causes the automatic rotation of the tissue cutter thereby generating a cut in the tissue 1628. In some embodiments, rotation of the cutter is performed by rotating the outer tube together with all the components inside of it.

In some embodiments, following the automatic rotation 1628, there is the automatic release of the proximal end of the implant 1630 by further retracting (moving proximally) the elongated body 104 from about 5 mm to about 9 mm, preferably 7 mm. In some embodiments, the release of the proximal end of the implant will allow the implant to unwind from the folded helical configuration (the folded configuration shown in FIG. 12*b*) into a curved configuration in which it is released and implanted into the cut (the curved configuration as shown in FIG. 12*d*). Since the release of the implant is performed in vicinity to the cut, the implant enters the cut. In some embodiments, the user then manually deflates the expandable body 1632. In some embodiments, optionally the user then assesses the insertion of the implant in the cut 1634. In some embodiments, the user then presses the button for the fourth time 1636, which causes the automatic insertion of the operational head in the outer tube optionally together with the tissue cutter 1638. In some embodiments, optionally the user then assesses (again if done before or for the first time if not performed before) deployment of the implant in the cut 1640. In some embodiments, the method ends by removing the device with the outer sheath from the patient 1642.

In some embodiments, valid to any of the methods disclosed herein, the rotational movement of the device, which performs the cutting, is concomitantly performed with the gradual release of the implant into the cut, therefore, at the end of the rotation the implant is completely released.

Exemplary Automatic Method Controlled by Controller

In some embodiments, the user (operator) controls the movement of the mechanisms by pressing on a single button that activates the controller to perform a synchronized step-by-step implant release method. In some embodiments, as mentioned above, the delivery system comprises of two controlled motors: a linear motor—moving the outer sheath (left to right and right to left, as explained above), and a rotary motor—moving the shaft assembly in a clockwise direction to create the circumferential cut inside the tissue. In some embodiments, the software in the controller also comprises instructions to control and synchronize the motor movement with the cutter.

The following Table A discloses an exemplary relationship between the actions of the linear motor, the rotary motor, the parts of the device and the action of the implanting method. The following Table A does not mean to be limiting and it is brought to allow a person having skills in the art to understand the invention.

TABLE A

| Stage | Linear motor | Rotary motor | Part that moves | Action performed | Method action |
|---|---|---|---|---|---|
| User presses button | | | | | |
| 1 | On | Off | Elongated body 104 | Moves backwards (proximally) | Exposing operational head |
| 2 | On | Off | Elongated body 104 | Moves backwards (proximally) | Releasing implant distal end |
| User inflates expandable body and presses button - or optionally inflation is performed automatically. | | | | | |
| 3 | Off | On | Shaft 302 rotates and cutter with it | Clockwise rotation | Cutting tissue |
| 4 | On | Off | Elongated body 104 | Moves backwards (proximally) | Releasing implant proximal end |
| Optionally, the system stops to allow user to assess correct insertion of implant and then user presses button | | | | | |
| User deflates expandable body - or optionally deflation is performed automatically. | | | | | |
| 5 | On | Off | Elongated body 104 | Moves forward (distally) | Covering operational head |
| Optionally, device disables use of button | | | | | |

Exemplary Emergency Stop Button

In some embodiments, the device comprises at least one emergency button configured to stop the action that the device is performing at that moment. In some embodiments, pressing the emergency button once stops the action that is performed in that moment. In some embodiments, pressing the emergency button twice causes the device to completely retract inside the shaft, including when relevant but not exclusively, deflating the expandable body, retracting the cutter, rotating to insert the implant inside the shaft.

Exemplary Visual Indications to the User

In some embodiments, after each time that the user presses a button, a visual indication is shown to the user to let him know that the automatic actions are finished and that the next step in the method can be performed. In some embodiments, visual indications can be led light of a variety of colors. In some embodiments, visual indications can be a digital screen.

Exemplary Non-Urethral Use

In some embodiments, the device and methods of implantation are used for other parts of the body that require opening of a tubular member or any other body lumen, for example the digestion system, the vascular system, etc.

Various embodiments and aspects of the present invention as delineated hereinabove and as claimed in the claims section below find support in the following examples.

Example of Operating Instructions for Use of the Device

For some embodiments, the apparatus described herein is used in conjunction with one or more of the following pieces of equipment:

380 mm, 2.9 mm, 12° telescope (CL-SCOPE)
24 F sheath (CL-SHEATH)
Visual Obturator (CL-VO)
Cystoscopy camera, light box/cable and monitor
Olympus ESG-400 Universal HF generator
Standard fluid irrigation system including new, sterile fluid tubing
Standard endoscopic grasper kit For some such embodiments, the operating instructions for use of the apparatus include one or more of the following steps. It is noted that these steps are provided purely by way of example, and that some or all of these steps are not necessarily implemented.

1. Pre-Procedure Cystoscopy
   1.1 Assemble the 2.9 mm 12° telescope (CL-SCOPE), visual obturator (CL-VO), and 24 F (CL-SHEATH).
   1.2 Advance the telescope assembly through the urethra and visualize both the urethra and bladder by advancing into the bladder.
   1.3 Remove the telescope and visual obturator, leaving the sheath in the bladder.

2, Preparation
   2.1 Confirm that packaging components are unopened and undamaged.
   2.2 Inspect all components for any damage that may have occurred during shipment or other handling.
   2.3 While holding the handle end (heavy end) of pouch, open the pouch by peeling the sides (device handle end) to access the sterile contents.
   2.4 Using sterile technique, remove the plastic tray out of the pouch.
   2.5 Using sterile technique, remove the device from the packaging by grasping the handle and pulling the device out of the tray the tray.
   2.6 Inspect the device tip and confirm that the distal balloon is not visible.
   2.7 Connect the Delivery System to the auxiliary equipment as follows:
   1. Insert 2.9 mm 12° telescope (CL-SCOPE) into device with the telescope lightpost at 6 o'clock. Keep forward pressure on the telescope, hold telescope lightpost at 6 o'clock, and secure the scope by pressing the scope in until a "click" is felt.
   2. Connect the cystoscope camera on the telescope and light source to the lightpost connector
   3. Connect the power cable to the power supply
   4. Connect the blue electrode connector to the Olympus ESG-400 Universal HF generator and set to BLEND-CUT 50 setting
   5. Insert the delivery system through the outer sheath (CL-SHEATH)

3. Device Insertion and Positioning
   3.1 Distal Tip partial exposure by pressing the button (Step 1-1$^{st}$ button press), Dilatation Balloon Exposure for increase field of view.

3.2 Locate the treatment site by visualizing the prostatic fossa from the bladder neck to the verumontanum.

3.3 Partial Implant Release by pressing the button (Step 2-2$^{nd}$ button press), initial deploying of the implant and cutting element exposure. The flexible Nitinol implant extends 33 mm from the side of the distal of the dilatation balloon.

3.4 To avoid external prostatic structures (e.g., neurovascular bundles), position the Delivery Device tip in the anterior aspect of the prostate in either the 2-3 or 9-10 o'clock position. Orient the tip to 12 o'clock to ensure the implant deploys the center between the two lateral lobes (implant deploys around the dilatation balloon.

As with cystoscopy, keep device parallel to the prostatic fossa and avoid excessive instrument movement throughout positioning and deployment.

To obtain the desired urethral opening, place implants throughout the length of the lateral prostate lobes at approximately 1 cm to 1.5 cm intervals starting 1.5 cm distal to the bladder neck.

3.5 Position the Delivery Device such that the Marker is against the target prostatic middle section lobe in the lateral upward direction.

3.6 To achieve desired amount of urethral opening, angle the Delivery Device to 6 o'clock and push the distal end upward, applying slight pressure to the Delivery Device tip via Delivery Device handle.

4. Implant Deployment

While holding the Delivery Device distal tip stable against the target tissue, perform the following steps:

4.1 Inflate the dilatation balloon with the pressure control syringe (FIGS. 4*a* and 4*b*) up to 2 atm. Make sure dilatation balloon is fully inflated by visualization of the inflated balloon on the screen monitor.

4.2 Trigger Urethral Implant Release sequence by pressing the button (Step 3-3$^{rd}$ button press), creating a circumferential urethral cut inside the prostate and deploying nitinol implant inside the created cut. The System circumferential urethral cut is up to 5 mm deep inside the prostate gland tissue which is sufficient to reliably position the prostatic implant inside the cut based on cadaver and clinical studies.

4.3 After the implant is fully deployed, hold still for up to 10 seconds, deflate the dilatation balloon by creating a vacuum pressure until syringe is filled up to 40 cc while holding it upward.

4.4 To withdraw the delivery device and press the button (Step 4-4$^{th}$ button press) to cover the distal end assembly. The Delivery Device can then be removed from the cystoscopy sheath. Gently pull the delivery device with light force in back-and-forth movements. As with cystoscopy, keep the device parallel to prostatic fossa. When advancing the Delivery Device distally, maintain the Delivery Handle and in the center between the lobes.

4.5 To deploy an additional implant, remove Delivery Device from the sheath and replace with a new System.

To obtain the desired urethral opening, place implants throughout the length of the urethral prostate at approximately 1 cm intervals.

4.6 Cystoscopy may be performed in between and/or after implant deployments to cystoscopically address if any additional implants are needed. If an additional implant is needed, see section 4, Delivery Device Positioning: Lateral Lobe. If no obstruction persists, continue to section 6, Cystoscopy.

5. Cystoscopy

Between and after implant deployments, perform a cystoscopy of the urethra and bladder to:

Confirm the desired effect has been achieved.

Confirm that all implant components are well embedded inside the mucosal tissue within the prostatic urethra.

Ensure implants are not present in the bladder or at the bladder neck extending into the bladder vesicle.

Assess the trigone and bladder for any damage.

If required, using a foreign body retrieval grasper or other applicable instrument, remove:

Improperly placed implants (i.e. implants placed within the bladder or exposed to stagnant urine)

Implants not well apposed to tissue (i.e. untensioned implants or any loose implant components/device components)

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer and may not be feasible or practical for performing purely manually, by a human expert. A human expert who wanted to manually perform similar tasks, such as manually operate an implant device, might be expected to use completely different methods, e.g., making use of expert knowledge and/or the pattern recognition capabilities of the human brain, which would be vastly more efficient than manually going through the steps of the methods described herein.

The invention claimed is:

1. An apparatus comprising:

a device for treatment of a urethra that is constricted due to benign prostatic hyperplasia (BPH), the device comprising:

a delivery tool having a proximal portion and a distal portion, the distal portion configured to be advanced to a location in an area of the urethra that is to be treated, and the distal portion comprising:

an expandable element that is configured to expand within the urethra such as to enlarge the urethra in the area to be treated, the expandable element defining an outer surface;

a tissue cutter disposed outside the outer surface of the expandable element, the tissue cutter configured to form a cut in an inner surface of the urethra, subsequent to the expandable element having expanded such as to dilate the urethra; and an implant configured to maintain the urethra in a dilated state, by being implanted within the cut in the inner surface of the urethra, the implant comprising two end sections and a middle section disposed between the two end sections, and the implant being shaped such that in an unconstrained configuration of the implant, the middle section is substantially straight;

wherein a length of the middle section of the implant is at least 50% of a length of the implant.

2. The apparatus according to claim 1, wherein the implant is configured to be implanted within the cut in the inner surface of the urethra such that the middle section of the implant is constrained into a curved shape.

3. The apparatus according to claim 1, wherein the implant is configured to be maintained in a spiral shape, while the implant is disposed within the delivery tool.

4. The apparatus according to claim 1, wherein the implant has a length of 40-80 mm.

5. The apparatus according to claim 1, wherein the implant has a thickness of 0.01-1 mm.

6. The apparatus according to claim 1, wherein the implant has a width of 0.5-4 mm.

7. The apparatus according to claim 1, wherein the tissue cutter has a length of 3-10 mm.

8. The apparatus according to claim 1, wherein the tissue cutter is configured to form the cut at an angle of 90 degrees with respect to a longitudinal axis of the delivery tool.

9. The apparatus according to claim 1, wherein the tissue cutter is configured to form the cut at an angle other than 90 degrees with respect to a longitudinal axis of the delivery tool.

10. The apparatus according to claim 1, wherein the expandable element has a length of 3-100 mm.

11. The apparatus according to claim 1, wherein the expandable element is configured to be inflated to an internal pressure of 1-20 atm.

12. The apparatus according to claim 1, wherein the expandable element comprises a balloon.

13. The apparatus according to claim 1, further comprising one or more implant carrier arms extending from a shaft of the delivery tool and being disposed outside the outer surface of the expandable element.

14. The apparatus according to claim 13, wherein the one or more implant carrier arms are configured to release the implant into the cut.

15. The apparatus according to claim 13, further comprising one or more implant holders coupled to the one or more implant carrier arms, and wherein:

the implant is configured to be disposed between the one or more implant carrier arms and the one or more implant holders such that the implant is held in place by the one or more implant carrier arms and the one or more implant holders; and the one or more implant holders being configured to be retracted proximally with respect to the one or more implant carrier arms such that the implant is configured to be released by the one or more implant carrier arms into the cut within the urethra, to thereby maintain the urethra in the dilated state.

16. The apparatus according to claim 13, wherein the delivery tool further comprises an optical element, and wherein the one or more implant carrier arms and the expandable element are configured so as to allow the optical element to visualize the urethra.

17. A method for treating a urethra that is constricted due to benign prostatic hyperplasia (BPH) comprising:

identifying a constricted area of the urethra requiring treatment;

inserting into the urethra a delivery tool that includes an expandable element that defines an outer surface, and a tissue cutter disposed outside the outer surface of the expandable element;

using the delivery tool, delivering, to the identified constricted area of the urethra, an implant that has two end sections and a middle section disposed between the two end sections, a length of the middle section of the implant being at least 50% of a length of the implant, and the implant being shaped such that in an unconstrained configuration of the implant, the middle section is substantially straight;

expanding the urethra by expanding the expandable element in the identified constricted area of the urethra;

subsequently, forming a cut in an inner surface of the urethra using the tissue cutter; and releasing the implant into the cut to maintain the urethra in a dilated state.

18. The method according to claim 17, wherein delivering the implant to the identified constricted area of the urethra comprises delivering the implant while the implant is compressed into a spiral configuration.

19. The method according to claim 17, wherein releasing the implant into the cut to maintain the urethra in the dilated state, comprises releasing the implant into the cut while the middle section of the implant is constrained into a curved shape.

20. The method according to claim 17, wherein the delivery tool further includes one or more implant carrier arms extending from a shaft of the delivery tool and being disposed outside the outer surface of the expandable element, and wherein delivering the implant to the identified constricted area of the urethra comprises delivering the implant while the implant is in a removably coupled state with respect to the one or more implant carrier arms.

21. The method according to claim 20, wherein releasing the implant into the cut comprises releasing the implant from the one or more implant carrier arms.

22. The method according to claim 20, wherein the delivery tool further includes one or more implant holders coupled to the one or more implant carrier arms, and wherein delivering the implant to the identified constricted area of the urethra comprises delivering the implant while the implant is held in place with respect to the one or more implant carrier arms by being disposed between the one or more implant carrier arms and the one or more implant holders.

23. The method according to claim 22, wherein releasing the implant into the cut comprises retracting one of the one or more implant holders proximally with respect to one of the one or more implant carrier arms.

24. The method according to claim 22, wherein releasing the implant comprises releasing a distal portion of the implant prior to expanding the expandable element and releasing a proximal portion of the implant subsequently to expanding the expandable element.

25. An apparatus comprising:

a device for treatment of a urethra that is constricted due to benign prostatic hyperplasia (BPH), the device comprising:

a delivery tool having a proximal portion and a distal portion, the distal portion configured to be advanced to a location in an area of the urethra that is to be treated, and the distal portion comprising:

an expandable element that is configured to expand within the urethra such as to enlarge the urethra in the area to be treated, the expandable element defining an outer surface;

a tissue cutter disposed outside the outer surface of the expandable element, the tissue cutter configured to form a cut in an inner surface of the urethra, subsequent to the expandable element having expanded such as to dilate the urethra;

an implant configured to maintain the urethra in a dilated state, by being implanted within the cut in the inner surface of the urethra, one or more implant carrier arms extending from a shaft of the delivery tool and being disposed outside the outer surface of the expandable element; and one or more implant holders coupled to the one or more implant carrier arms, wherein:

the implant is configured to be disposed between the one or more implant carrier arms and the one or more implant holders such that the implant is held in place by the one or more implant carrier arms and the one or more implant holders; and the one or more implant holders are configured to be retracted proximally with respect to the one or more implant carrier arms such that the implant is configured to be released by the one or more implant carrier arms into the cut within the inner surface of the urethra, to thereby maintain the urethra in the dilated state.

26. A method for treating a urethra that is constricted due to benign prostatic hyperplasia (BPH) comprising:

identifying a constricted area of the urethra requiring treatment;

inserting into the urethra a longitudinal delivery tool that includes:

an expandable element that defines an outer surface, a tissue cutter disposed outside the outer surface of the expandable element, one or more implant carrier arms extending from a shaft of the delivery tool, and one or more implant holders coupled to the one or more implant carrier arms, and an implant disposed between the one or more implant carrier arms and the one or more implant holders such that the implant is held in place by the one or more implant carrier arms and the one or more implant holders;

delivering the implant for deployment at the identified constricted area of the urethra;

releasing a distal portion of the implant by retracting one of the one or more implant holders proximally with respect to one of the one or more implant carrier arms;

expanding the urethra using the expandable element at the identified constricted area of the urethra;

forming a cut in an inner surface of the urethra; and releasing a proximal portion of the implant by retracting one of the one or more implant holders proximally with respect to one of one or more implant carrier arms, thereby releasing the implant into the cut in the inner surface of the urethra.

* * * * *